(12) United States Patent  
Kontaxis et al.

(10) Patent No.: US 11,419,680 B2  
(45) Date of Patent: Aug. 23, 2022

(54) PATIENT SPECIFIC 3-D INTERACTIVE TOTAL JOINT MODEL AND SURGICAL PLANNING SYSTEM

(71) Applicant: New York Society for the Relief of the Ruptured and Crippled, Maintaining the Hospital for Special Surgery, New York, NY (US)

(72) Inventors: Andreas Kontaxis, New York, NY (US); Lawrence Gulotta, Chappaqua, NY (US)

(73) Assignee: New York Society For The Relief Of The Ruptured And Crippled, Maintaining The Hospital For Special Surgery, New York, NY (US)

(*) Notice: Subject to any disclaimer, the term of this patent is extended or adjusted under 35 U.S.C. 154(b) by 796 days.

(21) Appl. No.: 16/338,275

(22) PCT Filed: Oct. 6, 2017

(86) PCT No.: PCT/US2017/055589  
§ 371 (c)(1),  
(2) Date: Mar. 29, 2019

(87) PCT Pub. No.: WO2018/067966  
PCT Pub. Date: Apr. 12, 2018

(65) Prior Publication Data  
US 2020/0030034 A1  Jan. 30, 2020

Related U.S. Application Data

(60) Provisional application No. 62/405,814, filed on Oct. 7, 2016, provisional application No. 62/426,081, filed on Nov. 23, 2016.

(51) Int. Cl.  
*A61B 34/10* (2016.01)  
*A61F 2/30* (2006.01)  
(Continued)

(52) U.S. Cl.  
CPC ............ *A61B 34/10* (2016.02); *A61F 2/3094* (2013.01); *A61F 2/4081* (2013.01); *A61F 2/46* (2013.01);  
(Continued)

(58) Field of Classification Search  
CPC ...... A61B 34/10; A61F 2/3094; A61F 2/4081; A61F 2/28  
See application file for complete search history.

(56) References Cited

U.S. PATENT DOCUMENTS 6,801,801 B1  10/2004  Sati  
2005/0065617 A1  3/2005  Moctezuma de la Barrera et al.  
(Continued)

FOREIGN PATENT DOCUMENTS

JP  2013503007 A  1/2013  
JP  2014516594 A  7/2014  
(Continued)

OTHER PUBLICATIONS

Chen et al.; Version Correction Comprises Remaining Bone Quality After Eccentric Reaming in B2 Glenoids; Journal of Shoulder and Elbow Surgery; 26(5); pp. e158-e159; May 1, 2017.  
(Continued)

*Primary Examiner* — Jason-Dennis N Stewart  
(74) *Attorney, Agent, or Firm* — Shay Glenn LLP

(57) ABSTRACT

Methods, systems and devices for pre-operatively planned total or partial joint surgery including, for example, anatomic and reverse shoulder surgery guides and implants. There are also methods for pre-operative planning methods for designing glenoid implants and prostheses, particularly with patient-specific augmentation, based on considerations of multiple factors affecting the outcome of a selected reverse or anatomic shoulder surgery. There are also described methods of performing total or partial joint sur-  
(Continued)

gery, including anatomic or reverse shoulder surgery, using surgery guides and implants in patients undergoing joint surgery.

20 Claims, 13 Drawing Sheets

(51) Int. Cl.
*A61F 2/40* (2006.01)
*A61F 2/46* (2006.01)
(52) U.S. Cl.
CPC ... *A61B 2034/102* (2016.02); *A61B 2034/108* (2016.02); *A61F 2002/30952* (2013.01); *A61F 2002/30985* (2013.01)

(56) References Cited

U.S. PATENT DOCUMENTS

| | | |
|---|---|---|
| 2006/0095047 A1 | 5/2006 | de la Barrera |
| 2007/0250174 A1 | 10/2007 | Tornier et al. |
| 2009/0164024 A1 | 6/2009 | Rudan et al. |
| 2010/0125336 A1 | 5/2010 | Johnson et al. |
| 2010/0211178 A1 | 8/2010 | Nogarin et al. |
| 2011/0130795 A1 | 6/2011 | Ball |
| 2012/0109137 A1 | 5/2012 | Iannotti et al. |
| 2012/0109226 A1 | 5/2012 | Iannotti et al. |
| 2012/0143267 A1 | 6/2012 | Iannotti et al. |
| 2013/0066321 A1 | 3/2013 | Mannss et al. |
| 2013/0110116 A1 | 5/2013 | Kehres et al. |
| 2013/0110470 A1 | 5/2013 | Vanasse et al. |
| 2014/0081342 A1 | 3/2014 | Iannotti et al. |
| 2014/0107654 A1 | 4/2014 | Kehres et al. |
| 2014/0107715 A1 | 4/2014 | Heilman et al. |
| 2014/0257304 A1 | 9/2014 | Eash |
| 2015/0223941 A1 | 8/2015 | Lang |
| 2016/0045317 A1 | 2/2016 | Lang et al. |
| 2016/0120555 A1 | 5/2016 | Bonin, Jr. et al. |
| 2016/0217268 A1 | 7/2016 | Otto et al. |
| 2016/0228234 A1 | 8/2016 | Hansen et al. |
| 2016/0270854 A1 | 9/2016 | Chaoui |

FOREIGN PATENT DOCUMENTS

| | | |
|---|---|---|
| WO | WO2013/060851 A1 | 5/2013 |
| WO | WO2015/071757 A1 | 5/2015 |

OTHER PUBLICATIONS

Kontaxis et al.; Humeral Version in Reverse Shoulder Arthroplasty Affects Impingement in Activities of Daly Living; Journal of Shoulder and Elbow Surgery; 26(6); pp. 1073-1082; Jun. 1, 2017.

Tempelaere et al; Dynamic Three-Dimensional Shoulder MRI During Active Motion for Investigation of Rotator Cuff Disease; PloS one; 11(7); e0158563; Jul. 19, 2016.

Wylie et al.; Planning Software and Patient-Specific Instruments in Shoulder Arthroplasty; Current Reviews in Musculoskeletal Medicine; 9(1); pp. 1-9; Mar. 1, 2016.

Kontaxis et al.; How Computer Models Can Help Prosthesis Implantation with the Best Mobility and Minimum Impingement; Hospital for Special Surgery, New York, NY; 2016.

Kontaxis et al.; Pre-Operative Planning and Accurate Implantation Can Increase Free Range of Motion in Reverse Shoulder Arthroplasty; Cadaveric Validation; Hospital for Special Surgery; New York, NY; 2016.

400

405

Output patient specific assessments for all anatomic shoulder procedures evaluated, including bone quality, tissue impingements, forces generated and how borne by the implant, muscle performance, bone impingements, wear, soft tissue balancing, etc for selected activity of daily living and standard clinical tests for all selected prosthesis manufacturer, models and sizes

410

Output patient specific assessments for all reverse shoulder procedures evaluated, including bone quality, tissue impingements, forces generated and how borne by the implant, muscle performance, bone impingements, wear, soft tissue balancing etc for selected activity of daily living and standard clinical tests for all selected prosthesis manufacturer, models and sizes

415

Surgeon reviews evaluated shoulder procedures based on a number of factors such as joint contact force and stability, muscle force, patient specific wear, kinematic factors of impingement, mechanical stability, fixation strength, soft tissue factors of comprehensive shoulder prosthesis function, standardized clinical tests, clinical assessment of patient health factors, patient prioritized activities of daily living and other characteristics and qualities used to evaluate suitable surgical options and prosthesis elected for this patient, as well as provide for modification of any evaluated plans.

420

Based on decision above, output Plan for Surgery (order implants, obtain any 3D printed or other patient specific implants or guides, operating room and patient scheduling, etc) and optional assessment reports for use with patient consultation, information and informed consent

FIG. 4

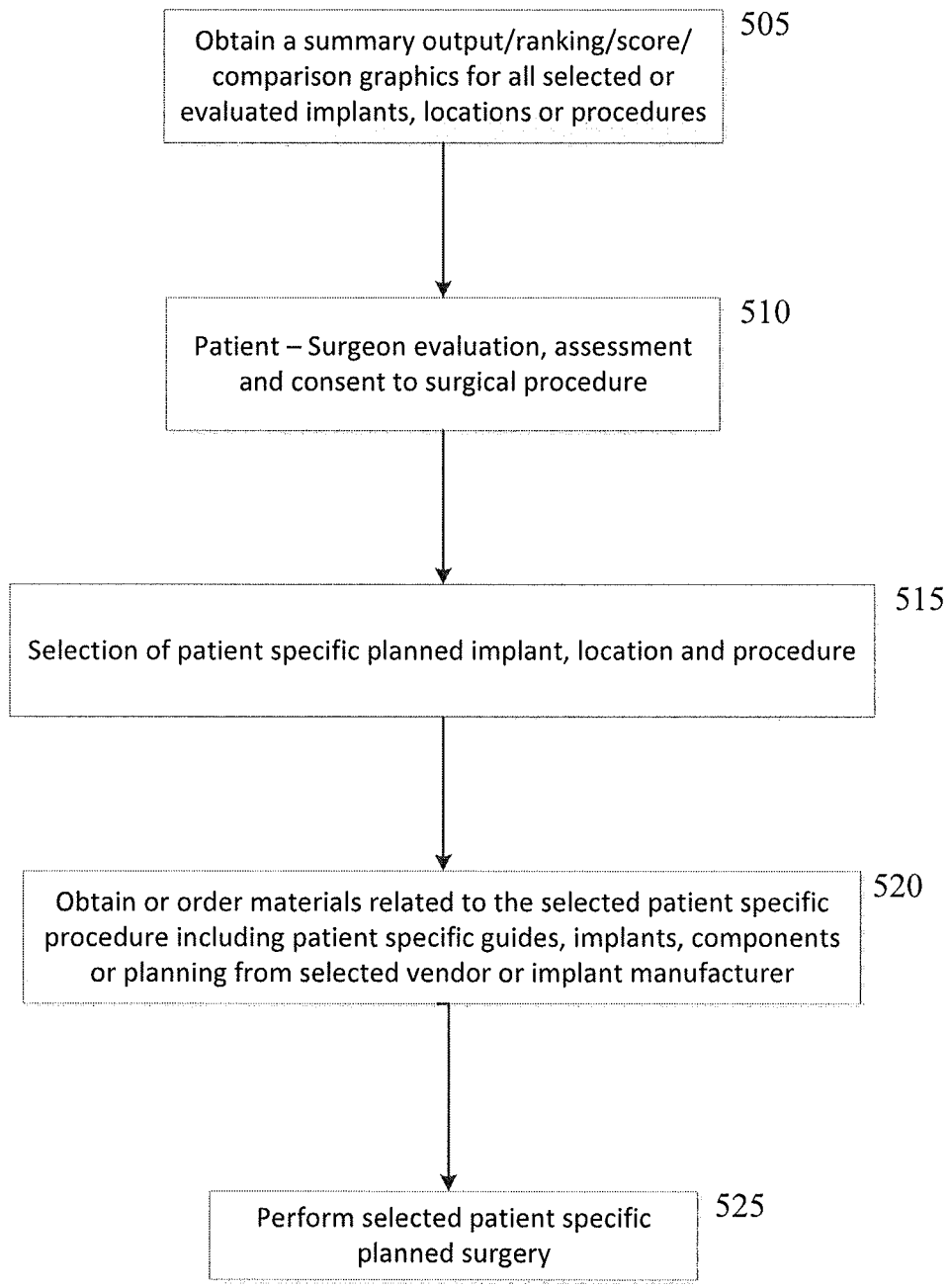

TABLE 808

| | | Digital/Virtual Model Data | | | | |
|---|---|---|---|---|---|---|
| | | Component/implant | Guide | PSI | Instruments | Plug in planning |
| MFG A* | Reverse | ✓ | | | | |
| | Anatomic | ✓ | ✓ | | | |
| MFG B* | Reverse | ✓ | ✓ | ✓ | ✓ | ✓ |
| | Anatomic | ✓ | ✓ | | ✓ | |
| MFG C* | Reverse | ✓ | ✓ | | | |
| | Anatomic | ✓ | | ✓ | ✓ | |
| MFG D* | Reverse | ✓ | | ✓ | ✓ | ✓ |
| | Anatomic | ✓ | ✓ | ✓ | ✓ | ✓ |

Optional* MFG virtual models obtained by 3D scan/remodels model not provided by MFG

| Patient Name | Scorecard/Grade Assessment output module | | | | | | |
|---|---|---|---|---|---|---|---|
| Procedure | A | | | B | | C | |
| Reverse | | | | | | | |
| Anatomic | | | | | | | |
| | R | S | A | R | S | A | |
| | R | S | A | R | S | A | |

Assessment Criteria*
Range of Motion (ROM) = R
Stability (STAB) = S
Activites of Daily Living (ADL) = A

*Prioritized by patient and/or surgeon

FIG. 8C

PATIENT SPECIFIC 3-D INTERACTIVE TOTAL JOINT MODEL AND SURGICAL PLANNING SYSTEM

CROSS REFERENCE TO RELATED APPLICATIONS

This application claims priority to U.S. Provisional Patent Application No. 62/405,814, filed Oct. 7, 2016, titled "PATIENT SPECIFIC 3-D INTERACTIVE SHOULDER MODEL AND SURGICAL PLANNING SYSTEM," U.S. Provisional Patent Application No. 62/426,081, filed Nov. 23, 2016, titled "PATIENT SPECIFIC 3-D INTERACTIVE SHOULDER MODEL AND SURGICAL PLANNING SYSTEM" each of which is incorporated herein by reference in its entirety.

FIELD

The presently disclosed subject matter relates to methods, systems and devices for virtual pre-operatively planned implants and prostheses for use in comparison and planning of total joint arthroplasty. More particularly, shoulder implants and prostheses for use in comparison and planning of anatomic and reverse shoulder procedures are described. In addition, the presently disclosed subject matter also relates to the use of such implants and prostheses in patients undergoing a selected and planned partial or total joint surgery including anatomic or reverse shoulder surgery.

BACKGROUND

Shoulder replacement is a common surgical operation that has achieved positive results for many patients. Indeed, approximately 10% of joint replacement procedures globally are related to the shoulder. Many shoulder procedures are performed in a patient where substantially normally bone exists for orientation and fixation of a prosthetic replacement, or resurfacing. In these cases, the need for the shoulder replacement can often times be related mostly to the arthritic condition of the joint, and relative absence of healthy cartilage.

In some patients, however, one or more of the bones of the shoulder are not only arthritic, but have also had previous conditions that have caused bone to wear away. In such cases, there may not be sufficient bone to adequately affix a prosthetic implant to the bone, or the bones may have been worn such that the orientation of a joint replacement cannot be satisfactorily determined to ensure a positive patient outcome.

There are a number of factors that complicate the selection, orientation and affixation of prosthetic implant devices, such as glenoid implants and/or humeral implants. Failure to properly account for each factor can lead to improperly sized, misaligned and/or poorly affixed implants that result in a poor surgical outcome for the patient.

In order to increase the likelihood of successful patient outcomes in patients undergoing shoulder surgery, methods, systems and devices are needed that allow for the full understanding and incorporation of all necessary factors of a more comprehensive virtual modeling for optimization of shoulder implant selection and placement for comparison of reverse and anatomic shoulder surgery. Thus, a need remains for methods, systems and devices for pre-operatively planned shoulder surgery guides and implants, such as glenoid implants and prostheses that achieve desired outcomes for a selected anatomic or reverse shoulder procedure.

SUMMARY OF THE INVENTION

In general, in one embodiment, a computer implemented interactive patient specific surgical planning system for a method of performing a total joint or a partial joint surgery includes: (1) performing a virtual pre-operatively planned joint surgery to implant a prosthetic device; (2) accounting for a range of motion desired for activities of daily living and/or standard clinical assessments of range of motion after performing the virtual surgery; and (3) outputting results for each implant, each location, and each range of motion activity from each virtual surgery performed.

This and other embodiments can include one or more of the following features. The computer implemented interactive patient specific surgical planning system can further include instructions for anatomic or reverse shoulder surgeries. The computer implemented interactive patient specific surgical planning system can further include instructions for patient specific instruments for the surgical preparation and implantation of humeral and glenoid implants in patients undergoing reverse or anatomic shoulder surgery. The computer implemented interactive patient specific surgical planning system can further include steps for designing and/or creating implantable components for a patient specific anatomic or reverse shoulder procedure including a glenoid implant component, a humeral implant component, shoulder surgery guide, including a glenoid implant placement guide, a humeral implant placement guide based on pre-operative planning including patient specific bone, muscle and soft tissue along with glenohumeral joint, scapula, clavicle kinematics can further include one or more optimization steps. The computer implemented interactive patient specific surgical planning system can further include optimization steps including the identification of anatomic, surgical, procedural, range of motion, fixation, stabilization or other outcome risks based on measurements of one or more of a plurality of factors. The computer implemented interactive patient specific surgical planning system can further include instructions for a step in a pre-operative total joint planning method for comparison of anatomic or reverse shoulder surgery implants or guides where the anterior edge of a glenoid implant is aligned with an anterior edge of a glenoid bone. The computer implemented interactive patient specific surgical planning system can further include instructions for a step in a pre-operative total joint planning method for comparison of anatomic or reverse shoulder surgery implants or guides where the retroversion of a glenoid implant is adjusted. The computer implemented interactive patient specific surgical planning system can further include instructions for a step in a pre-operative total joint planning method for comparison of anatomic or reverse shoulder surgery implants or guides where the augmentation of a glenoid implant is adjusted. The computer implemented interactive patient specific surgical planning system can further include instructions for a step in a pre-operative total joint planning method for comparison of anatomic or reverse shoulder surgery implants or guides where the inferior tilt of a glenoid implant is adjusted. The computer implemented interactive patient specific surgical planning system can further include instructions for a step in a pre-operative total joint planning method for comparison of anatomic or reverse shoulder surgery implants or guides where bone support for a glenoid implant and/or a humeral implant is evaluated. The computer implemented interactive patient specific surgical planning system can further include instructions for a step in a pre-operative total joint planning method for comparison of anatomic or reverse shoulder surgery implants or guides where the medialization of a glenoid implant is adjusted by assessing the volumetric amount of bone needed to be removed by reaming. The computer implemented interactive patient specific surgical planning system can further include instructions for a step in a pre-operative total joint planning method for comparison of anatomic or reverse shoulder surgery implants or guides where fixation support in the absence of central pegs that penetrate a vault medially is analyzed. The computer implemented interactive patient specific surgical planning system can further include instructions for a step in a pre-operative total joint planning method for comparison of anatomic or reverse shoulder surgery implants or guides where a joint line is analyzed by comparing an original joint line and a new joint line. The computer implemented interactive patient specific surgical planning system can further include instructions for a step in a pre-operative total joint planning method for comparison of anatomic or reverse shoulder surgery implants or guides where widths of the glenoid implant and the glenoid bone are measured and matched after reaming and aligning inferior and superior axes of the glenoid implant and bone and including similar appropriate measuring and matching of the humeral implant. The computer implemented interactive patient specific surgical planning system can further include instructions for a step in a pre-operative total joint planning method for comparison of anatomic or reverse shoulder surgery implants or guides where the diameter of a humeral head is determined. The computer implemented interactive patient specific surgical planning system can further include instructions for a step in a pre-operative total joint planning method for comparison of anatomic or reverse shoulder surgery implants or guides where the height of a humeral head is determined. The computer implemented interactive patient specific surgical planning system can further include instructions for a step in a pre-operative total joint planning method for comparison of anatomic or reverse shoulder surgery implants or guides where the size of a humeral or glenoid implant is measured by computed tomography scan or other appropriate medical imaging modality. The computer implemented interactive patient specific surgical planning system can further include instructions for a step in a pre-operative total joint planning method for comparison of anatomic or reverse shoulder surgery implants or guides where a best fit size of a humeral implant or a glenoid implant from a range of sizes from one or more medical component manufacturers is determined. The computer implemented interactive patient specific surgical planning system can further include instructions for a step in a pre-operative total joint planning method for comparison of anatomic or reverse shoulder surgery implants or guides where vectors are compared in three dimensions to measure the distance of relocation of humeral tuberosity compared to the scapula. The computer implemented interactive patient specific surgical planning system can further include instructions for a step in a pre-operative total joint planning method for comparison of anatomic or reverse shoulder surgery implants or guides where range of motion analysis is conducted, including virtually positioning implants through extreme ranges of motion to measure impact locations and compensate for necessary functional range of motion based on activities of daily living and standard clinical assessments. The computer implemented interactive patient specific surgical planning system can further include instructions for a step in a pre-operative total joint planning method for comparison of anatomic or reverse shoulder surgery implants or guides where soft tissue analysis comprising determining key soft tissue insertion points is conducted. The computer implemented interactive patient specific surgical planning system can further include instructions for a step in a pre-operative total joint planning method for comparison of anatomic or reverse shoulder surgery implants or guides where penetration of the cortical wall anteriorly of the vault is assessed. The computer implemented interactive patient specific surgical planning system can further include instructions for a step in a pre-operative total joint planning method for comparison of anatomic or reverse shoulder surgery implants or guides where the width of the greater tuberosity to medial head edge with an implant is compared to the anatomic width. The computer implemented interactive patient specific surgical planning system can further include instructions for a step in a pre-operative total joint planning method for comparison of anatomic or reverse shoulder surgery implants or guides for viewing or displaying one or more anatomic views of indications of coronial, sagittal or transverse anatomical planes for the viewing of a glenoid implant or a humeral implant; views of a glenoid implant with patient-specific back-side augmentation; views of an exemplary glenoid implant with patient-specific augmentation; views of involved joint bone or a scapula bone and glenoid surface having depicted indicia of one or more factors assessed by the planning system for comparison; views of a scapula with a humerus bone having a selected implant and surgical procedure indicted; views of a glenoid implant with no back-side augmentation and view of a glenoid implant with back-side augmentation; and/or views of patient-specific humerus or glenoid implants each having views of customized affixation components.

In general, in one embodiment, a pre-operative planning method for a computer implemented interactive patient specific surgical planning system includes: (1) conducting pre-operative planning of a partial or a total joint surgery; (2) determining a best fit size of a joint implant; (3) conducting range of motion analysis including virtually positioning a joint implant under evaluation in a patient specific kinematic model of the joint; (4) conducting soft tissue analysis using the patient specific kinematic model of the virtually positioned joint implant; (5) assessing and adjusting characteristics of the joint implant within the patient specific kinematic model; and (6) selecting patient specific instruments for use with the selected joint implant based on the pre-operative analysis of the conducting steps.

This and other embodiments can include one or more of the following features. The method of conducting pre-operative planning can include one or more of analyzing a joint line, including comparing an original joint line and a new joint line, wherein the new joint line is substantially similar to the original joint line. The method of the step of conducting pre-operative planning can include comparing vectors in three dimensions which represent the distance and direction between tendon and muscle insertions on the scapula and the humerus for measuring the distance of relocation of humeral tuberosity compared to the scapula; determining the diameter of the humeral head; determining the height of humeral head; determining the size of humeral bone implant from digital images. The method of the step of determining a best fit size of a joint implant can include selecting a humeral implant from a range of sizes, wherein the range of sizes is selected from the group consisting of length of stem, size of humeral stem, diameter of stem, size diameter of head, height of head, and offset of the center spherical head compared to the center of the face of the humeral stem. The method of the step of conducting range of motion analysis can include simulating motion of the virtually implanted joint through extreme ranges of motion to measure impact locations and compensate for necessary functional range of motion. The method of the step of conducting soft tissue analysis can further include: determining key soft tissue insertion points, measuring distances in three dimensions for comparison to pre-operative conditions, and assessing lengths at extreme ranges of motion, such that total soft tissue length change or contraction is substantially maintained within anatomical ranges in order to substantially achieve most common activities of daily living. The method of the step of assessing and adjusting the characteristics of the joint implant can include: assessing and adjusting the thickness/height of the glenoid implant; assessing and adjusting the depth of the glenoid fossa; and assessing and adjusting the thickness of a graft. The method of the step of selecting patient specific instruments can include selecting a humeral implant and a glenoid implant based on the pre-operative analysis, or assessing and adjusting a humeral head, a glenoid thickness, a glenoid fossa depth, and a graft thickness based on the pre-operative analysis. The method can further include instructions for a comprehensive pre-operative total joint planning method for comparison of anatomic or reverse shoulder surgery implants or guides. The method can further include conducting range of motion analysis, including virtually positioning implants through extreme ranges of motion to measure impact locations and compensate for necessary functional range of motion. The method can further include conducting soft tissue analysis, including determining key soft tissue insertion points, measuring distances in three dimensions for comparison to pre-operative conditions, and assessing lengths at extreme ranges of motion, such that total soft tissue length change or contraction is substantially maintained within anatomical ranges in order to substantially achieve most common activities of daily living. The method can further include assessing and adjusting as needed the thickness/height of the glenoid implant. The method can further include assessing and adjusting as needed the depth of the glenoid fossa. The method can further include assessing and adjusting the thickness of a graft. The pre-operative planning can be done virtually based on images taken from a subject prior to surgery. The method can further include optimizing the dimensions of fixation elements of the glenoid implant using correspondence matrix between a three dimensional (3D) bony structure of the patient and a statistical shape based atlas according to the following steps: (1) developing a registration between patient bone and statistical shape model of the bone of interest; (2) extracting the principle modes representing the patient bone; (3) defining the fixation configuration, position or dimensions according to the corresponding modes; and (4) applying collision detection to confirm the configuration of the bone fixation. The method can further include identifying and comparing procedural risks between selected reverse or anatomic shoulder procedures by determining: whether a glenoid face coverage is maximized; whether an overhang of the glenoid face is minimized; whether bone removal on the glenoid face is minimized; whether the glenoid retroversion is less than about 5 to about 10 degrees; whether seating of the glenoid implant is greater than about 80% of the implant coverage area; whether there is minimized penetration of the glenoid cortical wall anteriorly; whether there is greater than about 3 mm bone thickness behind glenoid; whether the orientation offset between the native glenoid and implant superior/inferior axis is less than about 5 degrees; whether the superior or inferior tilt versus native glenoid is less than 5 degrees; whether there is an absence of a humeral head overhang compared to the cut, or prepared surface of the humeral bone; whether there is less than about 3 mm difference in humeral head diameter between anatomic and implant; whether there is less than about 1 mm difference in humeral head height between anatomic and implant; and whether there is less than about 2 mm greater tuberosity to medial head edge in comparison to anatomic; whereby procedural risks are identified; and the selection of prosthetic implants for the selected shoulder surgery are based at least in part on the identified procedural risks. The glenoid implant can be augmented to fit a patient for which pre-operative planning of an anatomic or reverse shoulder procedure was performed. The depth of augmentation, the size of augmentation, and/or the radial position of augmentation can vary depending on the pre-operative planning of a selected reverse or anatomic shoulder procedure. The augmentation can include a depth ranging from about 2 mm to about 4 mm. The augmentation can cover about 5%, 10%, 15%, 20%, 30%, 40% or 50% of the back side of the glenoid implant. The augmentation can covers about 50%, 60%, 70%, 80%, 90%, 95% or greater of the back side of the glenoid implant. The radial location of the augmentation on the backside of the glenoid implant can be selected from the group consisting of a posterior location, an anterior location, a superior location, an inferior location, and combinations thereof. The method can further include obtaining a patient specific shoulder surgery guide based upon the selected anatomic or reverse surgical method steps. The method can further include producing a shoulder surgery guide or a selected reverse or anatomic shoulder procedure, wherein producing the shoulder surgery guide comprises using a 3D printing device. The method can further include a selected anatomic or reverse shoulder procedure recommending prosthetic shoulder implants and placement positions, selected from the group consisting of adjustments in glenoid implant size, augmentation depth, augment position, positioning in six degrees of freedom, fixation type, fixation size, reaming depth, reaming diameter, reaming angle(s) and/or a combination thereof. The method can further include a computer readable medium having stored thereon executable instructions that when executed by the processor of a computer control the computer to perform one or more of the planning method steps or a selected reverse or anatomic shoulder procedure. The computer readable medium can have stored thereon executable instructions that when executed by the processor of a computer control the computer can generate a virtual three dimensional model of a glenoid implant reflecting one or more optimized parameters determined during pre-operative planning. The computer readable medium can have stored thereon executable instructions that when executed by the processor of a computer control the computer cam generate a virtual three dimensional model of a selected implant reflecting one or more optimized parameters determined during pre-operative planning for a selected reverse or anatomic shoulder procedure.

In general, in one embodiment, a pre-operative planning and shoulder surgery kit for a selected shoulder surgical procedure includes a set of instructions for performing pre-operative analysis steps and one or more guides, glenoid prosthetic devices and/or humeral prosthetic devices.

This and other embodiments can include one or more of the following features. The kit can further include a 3-D printing device for producing a guide and/or one or more glenoid and/or humeral prosthetic devices. The kit can further include a computer-readable medium for use in conducting the pre-operative planning, and designing a guide, glenoid implant and/or humeral implant based on input parameters gathered during the pre-operative planning. The devices can be customizable and/or modular in design such that the prosthetic device can be optimized for the patient based on the pre-operative planning analysis. The kit can include a range of glenoid implants having augmented back sides where the augmentation is selectable in terms of the augmentation size, shape, and position, both in the superior/inferior and posterior/anterior position. The kit can include a range of glenoid implants having augmented back is provided where the augmentation is selectable in terms of its size, shape, and position, where the position is defined by an angular and a radial position.

In general, in one embodiment, a computer implemented interactive patient specific surgical planning system includes obtaining a joint specific kinematic model of a joint of a patient to be evaluated for a total joint or a partial joint surgical procedure, operating a patient adaptation engine to modify at least one of bone, soft tissue or landmarks in the joint specific kinematic model to render a patient specific kinematic model by adapting the joint specific kinematic model to include one or more patient specific conditions, operating a prosthesis testing engine to electronically perform a total or a partial joint surgery to position a selected implant in the patient specific kinematic model and to simulate motion of the patient joint with the selected implant while performing an activity of daily living, providing an output of the results of the operating a patient adaptation engine and operating a prosthesis testing engine, and selecting an actual implant for a planned surgical procedure to be performed on the patient.

This and other embodiments can include one or more of the following features. The joint specific kinematic model can be one of a shoulder, a knee, a hip, an ankle, an elbow, a wrist, a hand or the joints of the fingers and thumb, and a foot or the joints of the toes. The one or more patient specific conditions can include a patient specific condition obtained from patient specific imaging, clinical evaluation, or testing. The system can further include modifying the kinematic model by applying one or more patient specific factors representing a bone characteristic. The system can further include modifying the kinematic model by applying one or more patient specific factors representing a ligament characteristic. The system can further include modifying the kinematic model by applying one or more patient specific factors representing a muscle characteristic. The system can further include modifying the kinematic model by applying one or more patient specific factors representing a soft tissue or cartilage or a joint capsule or a portion of a joint capsule or patient specific fibrous or scar tissue. The system can further include modifying the kinematic model by applying one or more patient specific factors representing one or more additional patient specific characteristics related to the total or partial joint surgery under evaluation. The operating a prosthesis engine step can be performed using a kinematic model. The system of the step of operating a prosthesis testing engine can further include the step of electing a digital model of a prosthesis for evaluation. The system can further include a step to position a model of the selected prosthesis using the surgical planning within the adapted patient specific kinematic model of the joint. The system can further include performing a virtual surgery to position the selected prosthesis within the patient specific kinematic model of the joint under evaluation. The system can further include the step of applying motion simulation of the patient specific kinematic model based on an activity of daily living wherein the selected prosthesis in the selected surgical location is evaluated while the motion of an activity of daily living is imparted to the patient specific model. The process of simulating the activities of daily living can be repeated for daily grooming, self-care and at least one athletic or sporting activity. The prosthesis can be moved to a different location within the patient specific kinematic model and the steps for additional simulations of activities of daily living are repeated. The system can further include providing an output from the prosthesis testing engine that includes the results of all simulations performed by the patient specific model including all implants tested, all surgical sites evaluated and the results of all motions imparted by simulated activities of daily living. A computer readable medium can be provided, having stored thereon executable instructions that when executed by the processor of a computer control the computer to perform steps comprising generating a virtual three dimensional model of a glenoid and/or humeral guide reflecting one or more optimized parameters determined during a pre-operative planning method. A computer readable medium can be provided, having stored thereon executable instructions that when executed by the processor of a computer control a 3D printing device in communication with the computer, whereby the 3D printing device prints a glenoid and/or humeral guide, or placement guide, for use in anatomic or reverse shoulder replacement surgery in a patient for which an optimization analysis was conducted. The system can further include a method of creating a reverse or anatomic shoulder surgery guide including utilizing one or more steps, analyses, optimizations and recommendations to create a patient specific shoulder surgery guide that includes automated design and creation of a three dimensional model of a glenoid and/or humeral guide reflecting one or more optimized parameters determined during a pre-operative planning step. Imaging data of a patient can be obtained from or based on images or scans taken from a patient prior to surgery wherein the imaging data is based on computed tomography (CT) imaging, x-ray imaging, positron emission tomography (PET) imaging or ultrasound imaging.

BRIEF DESCRIPTION OF THE DRAWINGS

Non-limiting and non-exhaustive embodiments of the various embodiments of the present invention are described with reference to the following drawings, wherein:

FIG. 4 is a flow chart of an exemplary computer implemented method of obtaining and comparing the results of simulations performed in FIGS. 2 and 3 to permit comparison of anatomic and reverse shoulder procedures for a patient.

FIG. 5 is a flow chart of an exemplary computer implemented method of providing outputs and evaluation of previous simulations and assessments in support of conducting the planned total or partial joint surgical procedure.

FIG. 8B is an exemplary virtual or digital component database for use with the total joint surgical planning and evaluation system of FIG. 8A.

FIG. 8C is an exemplary scorecard or assessment output provided by the total joint surgical planning and evaluation system of FIG. 8A.

DETAILED DESCRIPTION

Figure 1:
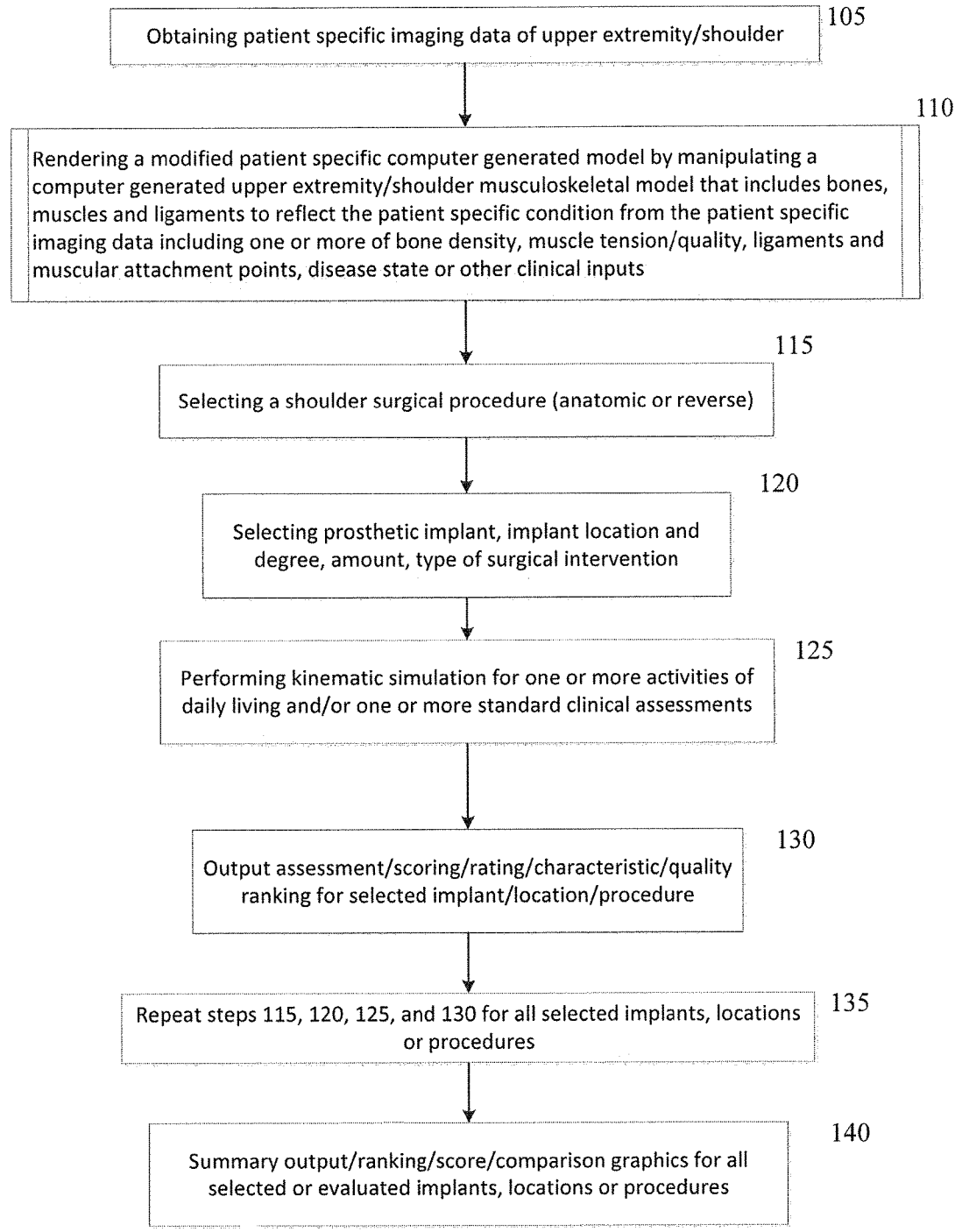
FIG. 1 is a flow chart of an exemplary computer implemented method of a total joint surgery planning and evaluation system.

Patients requiring shoulder surgery may have one or more of the bones of the shoulder that are not only arthritic, but may also have had previous conditions that have caused bone to wear away. In such cases, there may not be sufficient bone to adequately affix a prosthetic implant to the bone during a routine shoulder surgery. Indeed, the bones may have been worn such that the orientation of a joint replacement cannot be satisfactorily determined to ensure a positive patient outcome.

The glenoid bone can be subject to increased wear due to bone arthritic conditions of the joint, and due to alterations of a normal soft tissue envelope surrounding the joint. In such cases, the orientation of the face of the glenoid portion of the scapula bone may be altered so that the humeral bone is no longer appropriately opposed to the glenoid surface. In the case where the glenoid is severely worn, there can be two or more risks a surgeon must balance in an attempt to improve shoulder function and pain relief.

First, if the optimal orientation of the diseased but treated shoulder is not found and replicated with the prosthesis the patient may experience most operative complications related to subluxation or dislocation of the replaced shoulder joint. This can occur either due to passive inputs to the shoulder (e.g., leaning against it, or lying in bed), or due to active firing of surrounding soft tissue which is not able to be constrained by the replaced joint surfaces.

Additionally, the fixation of a replacement prosthesis, or implant, to the native patient bone can be problematic. Frequently, in order to counteract the risks associated with joint subluxation and dislocation described above, it can be necessary for a surgeon to orient or position the replacement prosthesis or implant in a position better suited to resist imbalanced muscle forces. In such cases, separation forces between the implant and the bone can increase, which in turn can increase the potential for loosening of the joint prosthesis in the bone. Implant loosening can be related to accelerated implant wear, bone erosion, increased tissue inflammation, joint synovitis, and pain.

In patients that have undergone shoulder replacement surgery, range of motion and strength are dependent on shoulder kinematics, which are in turn dependent on a host of factors. Such factor can, include for example, implant size, implant position, the design of implant shape, the joint line and soft tissue tension. In some cases it can be difficult to predict optimal implant size and position/orientation using currently available guides and implants. Often times a surgeon finds that there are too many variables to manage at one time. Moreover, the size choices of implants can be limited to the lowest practically functional groups to reduce economic burden to the health care system. Current implant designs and methodologies are inadequate to address these challenges because they are of significant cost, require time to develop, include increased risk of implant failure, and rely on human judgment of potential outcomes post-operatively.

There are many factors that can affect the optimal positioning of shoulder implants during replacement surgery. For example, such factors can include the patient size, relative bone wear, soft tissue strength and condition, six degrees-of-freedom positioning of the glenoid and/or the humeral prosthesis, selected implant size, preoperative patient activity and strength levels, post-operative treatment protocols, size and density of patient bone. Additional factors can include patient smoking status, concomitant handicaps and/or patient problems. It can be quite difficult for a surgeon to understand and balance these factors simultaneously. In addition, only a few of these factors are able to be controlled by the surgeon. Finally, each factor does not necessarily have an equally weighted impact on patient outcome. Nevertheless, it is considered that the implant size, position, orientation and bone preparation of the glenoid and the humerus can have a significant impact on the surgical outcomes.

A factor that further complicates, or makes more difficult, a surgeons task of optimally placing a replacement component or implant to counteract these risk is the fact that the condition of the scapula is such that few landmarks exists for the surgeon the comprehend the implant position within the bone. Thus, frequently a surgeon might find that the implant position is not replicating as was envisioned during the surgical intervention.

Others have attempted to improve a surgeon's chance of providing successful patient outcomes by providing operative techniques and tools. What is missing, however, is the ability to fully understand and incorporate multiple factors to optimize the implant selection and placement. Specifically, in some embodiments, the success of the surgery can be highly dependent on in the first instance, due consideration of an anatomic or reverse procedure followed then by both the selection of the matching prosthesis or prostheses (humeral and/or glenoid), as well as positioning of this prosthesis, as well as the soft tissue status before the surgery.

Disclosed herein are methods, systems and devices for pre-operatively planned shoulder surgery guides, including glenoid placement guides, and implants. Methods, systems and devices are provided for the replacement of the shoulder joint, such as the glenohumeral joint, wherein the conditions of the humeral and soft tissue envelop is taken into consideration. More specifically, what is considered is that the shape and position of the glenoid implant is not based solely on what can be seen and measured on the scapula, but can be chosen, designed, planned and placed with incorporation of the same information related to the humerus. After all, the shoulder is a two part joint, i.e. glenoid and humeral head, wherein both parts work in conjunction with one another, and the factors that affect performance of the device can in some embodiments include factors from both sides of the joint.

Appropriate sizing of the prosthesis can be important to successful outcomes, knowing that oversized or "overstuffed" replacement shoulders are more likely to dislocate, loosen, be painful, and/or have decreased range of motion. Replaced joints where the orientation of the prostheses is improper increases the likelihood of implant dislocation and loosening. Additionally, over-reaming, or too much bone removal, either on the glenoid, or the humerus, can be the cause of implant loosening, "under-stuffing" or inappropriate articular surface placement which can increase pain and decrease range of motion.

Provided herein are some embodiments is a shoulder implant evaluation criteria to assess match with the patient's anatomy, including optimal humeral and/or glenoid implant size and shape, and taking into account one or more of the following factors: assessment of the humeral implant fit to the humeral bone; relative hardness of the patient bone preoperatively; height and diameter of the humeral head placed on the humeral stem; orientation, or "offset" of the humeral head; and optimal bone removal for preservation of soft tissue insertion and attachment.

In some embodiments, a pre-operative planning method for designing and/or producing an augmented glenoid implant, humeral implant and/or a shoulder surgery guide for either or both of an anatomic shoulder procedure or a reverse shoulder procedure can comprise a number of comparisons within the computer rendered model to reflect one of more of the presence, location relative to other elements, attachment to other elements, physiologic quality or health of patient specific bone, muscle, tendon, and soft tissue within the surgical planning envelope including kinematic relationships and limitations to kinematics based on characteristics and factors of the above. In one specific example, there may be conducted within the surgical planning system electronic computer readable instructions for comparing vectors in three dimensions to measure the distance of relocation of humeral tuberosity compared to the scapula based on user or planning program selected prosthesis, surgical procedure or surgeon specified criteria.

In one specific example, an embodiment of a comprehensive surgical planning model may include 3 rotator cuff tendons that attach to the proximal humerus in the area of the greater tuberosity and the scapula along with, optionally, the patient specific health of the tendons, attachment point specifics as well as bone density/quality in potential implantation sites. These tendons control much of the rotation of the humerus about the scapula as well as having a part in elevating the humerus and representation of the movement of these tendons—as well as their potential role in load bearing, joint stabilization and other biomechanical factors—in subsequent multi-actions kinematic simulations of a planned surgical intervention through the a wide arrange of range of motion assessments including standard clinical range of motion and a number of motions related to activities of daily living. The activities of daily living may be a set of common activities for self-care as well as patient requested specific activities such as for occupation, sports, outdoor activities or recreational activities. Still further, using the various dynamic, interactive total joint computer planning methods described herein and enabled by the disclosed system, a patient and a surgeon may compare the projected range of motion, stabilization, fixation and longevity of a proposed surgical intervention—including a total joint arthroplasty procedure—based in part on a comparison of the above factors to determine long term surgical outcomes based on optimized range of motion of selected or patient determined activities of daily living based on the patient's intended return to an active post-surgical lifestyle.

In one aspect, the computer readable holistic total joint model—including modifications for patient specific factors—may be used to perform a number of operations and simulations to provide assessment, comparison and evaluation information for a wide array of evaluated anatomic or reverse shoulder procedures, prosthetics, implantation locations, surgical interventions to resolve one or more or a group of tendon changes, kinematics and kinetics of the glenohumeral joint (joint comprising the glenoid and humerus) including resulting simulated or predicted direction of force vectors, changing wear patterns and range of motion (ROM) of the implanted device versus the native joint including assessment of ROM for activities of daily living and standard clinical evaluations.

Additionally, in some embodiments, the computer enabled surgical planning and assessment system described herein permits users to change or modify or adjust the magnitude of one or more vectors by lengthening or increasing it with a joint prosthesis that is sized relatively larger for the joint to evaluate possible impact to or decrease of ROM, possible pain, and/or increased wear of the prosthetic components. In still another aspect, the computer enabled surgical planning and assessment system described herein permits users to change or modify or adjust the magnitude of one or more vectors by decreasing or shortening it with a joint prosthesis sized relatively smaller for the joint to permit assessment of potential or resulting unstable joint kinematics, increased probability of implant or joint dislocation as well as possible suboptimal mechanics for elevating the humerus. It is to be appreciated that one or more of a GUI, UI alone, in combination or used in conjunction with computer enabled operations and/or functions permit the various biomechanical, kinematic, wear, impingement, localization and other factors and variations described herein and utilized in this analysis to be accomplished virtually based on images taken from a subject or patient prior to surgery with all some or none of the various modifications described herein. Moreover, the computer enabled patient specific total joint surgical planning system also includes computer readable instructions to impart anatomically correct movement to the resulting virtually planned/simulated anatomical or reverse shoulder surgical procedure producing a virtual post-surgical model may to virtually cycled for movements representing once or repeated or activity of any selected duration or rate for one or more activities of daily living or standard clinical assessments, including patient specific modifications for activity for daily living.

FIG. 1 provides additional steps of an illustrative method 100. The method 100 includes representative steps 105-140 of an exemplary method of conducting a patient specific pre-surgical planning for an anatomic or reverse shoulder procedure.

In some embodiments, a pre-operative planning method utilizing the computer models described herein may be advantageous for designing and/or producing an augmented humeral implant and/or a shoulder surgery guide, an augmented glenoid implant and/or a shoulder surgery guide where range of motion (ROM) analysis and the wide range of other factors described herein can be conducted, including virtually positioning implants, surgical steps, as well as motion through ranges of motion commensurate with ADL to measure impact locations and compensate for or recommend adjustments to implant or location or surgical preparations to enhance a desired functional ROM outcome or to optimize ROM based on selection criteria to prioritize higher ROM for some selected activities for daily living, including patient specified post-surgical motions for selected activities of daily living. In some embodiments, this iterative analysis can be accomplished virtually based on images taken from a subject or patient prior to surgery. By measuring, assessing, evaluating and characterizing the resulting ROM and biomechanical and kinematic envelope with respect to glenoid implants and/or humeral implants used for selected anatomic or reverse shoulder procedures, data and information can be collected that informs the selection of an actual glenoid implant, an actual humeral head implant, and/or supports the design and production of one or more patient specific instruments including implant specific and patient specific cutting or surgical guides, and/or supports the creation of anatomic or reverse shoulder surgery guides or devices specific to the patient or subject to be treated.

In some embodiments, a pre-operative planning method for evaluating implants and surgical location as well as for use in designing and/or producing anatomic or reverse shoulder implants and/or a shoulder surgery guides can comprise one or more steps where soft tissue analysis is conducted virtually on one or more muscles, tendons, or ligaments. In some aspects, soft tissue analysis can comprise determining and/or assessing soft tissue removal, insertion, attachment or other characteristics of soft tissue expected in the planned procedure and thereafter analyzing impacts on and/or impacts from use of one or more implants (glenoid and/or humeral) or planned surgical procedures. In some embodiments, four rotator cuff muscles and their attachment points can be analyzed, or fewer rotator cuff muscles may be included in the post-surgical model simulation depending upon clinical or surgical assessment of the quality or characteristics of the soft tissue in question.

In some embodiments, the virtual total joint planning system permits a surgeon or user to adjust, diminish or remove soft tissue based on surgical technique or experience. In one aspect, a virtual analysis or interaction with the model may include the subscapularis and permit modification of an attachment point near the lesser tuberosity and also an attachment point near the anterior glenoid. In one aspect, a virtual analysis or interaction with the model may include the supraspinatus that attaches at an attachment point near the anterior greater tuberosity and above the scapular spine or shoulder blade. In still other aspects, a virtual analysis or interaction with the model may include soft tissue analysis including the infraspinatus that attaches at the greater tuberosity (posterior to supraspinatus) and below the scapular spine (posterior). In some aspects, a virtual analysis or interaction with the model may include soft tissue analysis including the teres minor that attaches posterior on the humerus and on the inferior scapular border.

In some embodiments, these and other soft tissue manipulations along with corresponding implants and surgical sites with their corresponding analysis can be accomplished virtually based on images taken from a subject or patient prior to surgery. It is believed that by analyzing in a more comprehensive way than has been previously proposed for a total joint assessment including the bones, biomechanical factors and kinematic interactions including the soft tissue around the glenohumeral joint, data and information can be collected that informs the selection between an anatomic shoulder procedure or a reverse shoulder procedure including for a selected procedure an appropriate glenoid implant, humeral implant and/or using information, data and analysis to support the design and production of a patient-specific implants, and/or supports the creation of a shoulder surgery guide device specific to the patient or subject to be treated based on the selected implant and procedure.

Turning now to a more specific discussion of FIG. 1 which provides additional steps of an illustrative method 100. The method 100 includes representative steps 105-140 of an exemplary method 100 of conducting a patient specific pre-surgical planning for replacement of a joint. The exemplary method 100 is described for a shoulder joint. In other aspects of the inventive method, the joint replacement planning methods and techniques described herein may be applied to other joints of the body to provide similar beneficial results of planning and simulating different prosthetic components based on kinematic models adapted to more accurately reflect patient anatomy and physiology including soft tissues. Moreover, the methods described herein are beneficial for providing insights into how long term use or wear of an implant based on kinematic and biomechanical actions from activities of daily living as applied to the proposed surgery. Exemplary other joints include, in addition to the shoulder, the hip, the elbow, the wrist, the ankle, the spine, the knee, the joints of the hand including the fingers and thumbs, and the joints of the feet including the toes. The illustrative example of method 100 is for an anatomic or reverse shoulder procedure.

First, at step 105, there is the step of obtaining patient specific imaging data of the upper extremity including the shoulder.

Next, at step 110, there is the step of rendering a modified patient specific computer generated model of the joint to be surgically modified. The modification includes various steps of manipulating a computer generated upper extremity/shoulder musculoskeletal model that includes bones, muscles and ligaments to reflect the patient specific condition. Modifications to the general computer model may be obtained from examination of the patient or other patient specific data including information obtained from the patient specific imaging data. Patient specific imaging data or other obtained patient data includes one or more of bone density, muscle tension/quality, ligaments and muscular attachment points, disease state or other clinical inputs. Additional patient joint specific soft tissue information or characteristics such as condition of cartilage or joint capsule may also be collected and indicated in the patient specific model.

Next, at step 115, there is the step of selected a joint based surgical procedure. In this example, the surgical decision involves shoulder surgery along with the decision for performing an anatomic shoulder surgery or a reverse shoulder surgery. The determination of anatomic or reverse is one of organization as the other surgical selection could be made as part of the additional actions assessed as part of step 135.

Next at step 120 is the step of selecting a prosthetic implant, an implant location and degree, amount, type of surgical intervention. This step includes the computer based or electronic alteration of the patient specific model to reflect the surgical modification to the joint to position and secure the selected prosthetic implant.

Next at step 125 is the step of performing kinematic simulation for one or more activities of daily living and/or one or more standard clinical assessments. This step provides information about the durability of the selected implant in the planned position as a variety of different motions are imparted to the modeled joint. The different motions relate to various activities of daily living including sports related activities and self-care activities among others to aid in determining the best fit implant and location. will Next at step 130 is the output of the results of the operation of the patient specific kinematic model based on those actions evaluated in step 125. This step provides an output assessment including scoring, rating, characteristic, quality ranking for the selected implant-location-procedure evaluated in step 125.

Next, at step 135, repeat steps 115, 120, 125, and 130 for all selected implants, locations or procedures for the patient specific joint surgery. In this way, information obtained from prior implant selections or proposed surgical locations may be further refined or altered in order to provide a range of suitable surgical options for consideration based on patient specific conditions and expected or desired post-surgical activities of daily living.

Finally, step 140 reflects the output of the method as an assessment of all tested implants and surgical locations. There is a summary output that includes the ranking, scoring, comparison graphics for all selected or evaluated implants, locations or procedures.

Figure 2:
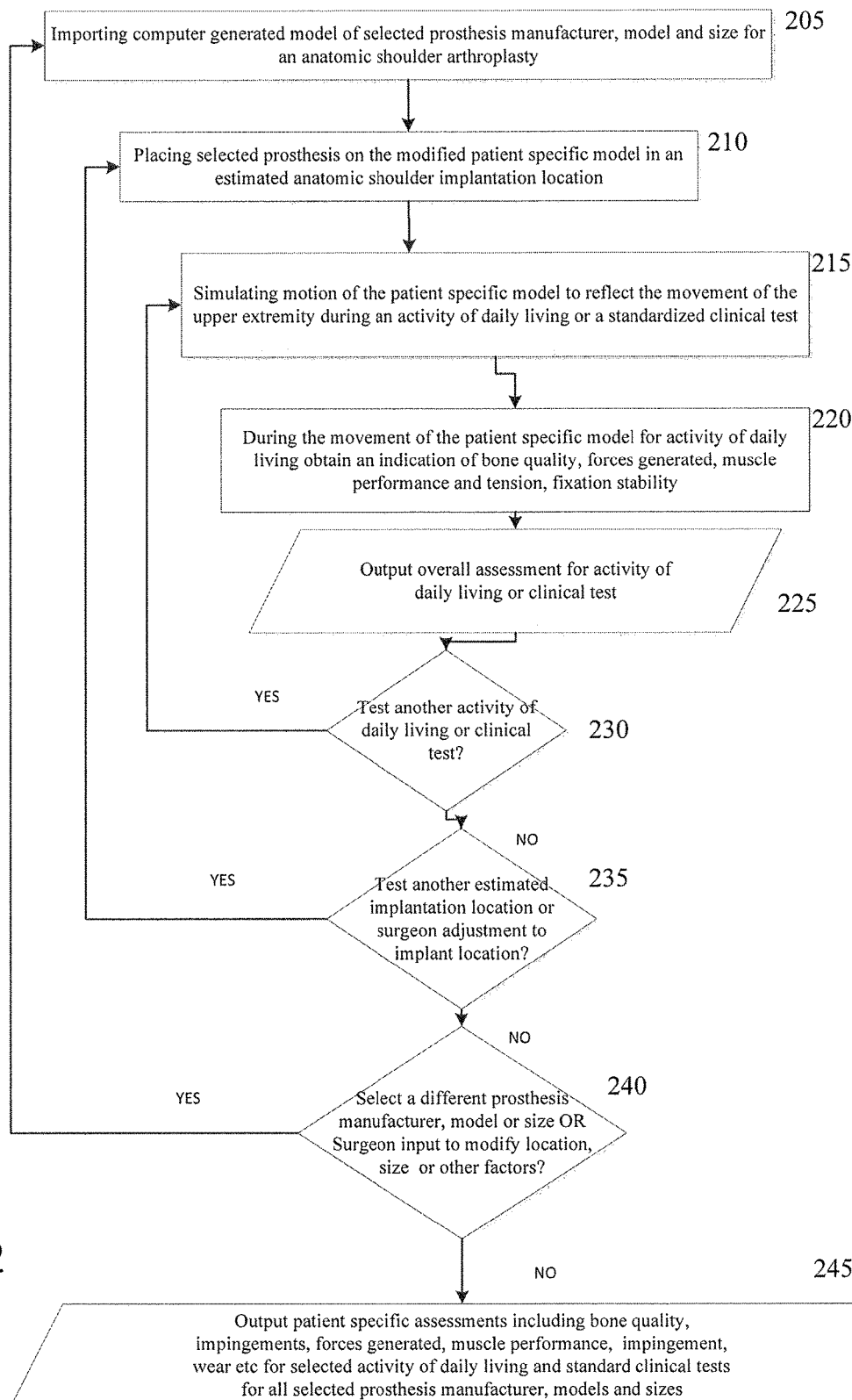
FIG. 2 is a flow chart of an exemplary computer implemented method of selecting, placing and testing an implant as part of a total joint surgery planning and evaluation system adapted for evaluation of an anatomic shoulder procedure.

FIG. 2 provides exemplary steps of an illustrative method 200 related to additional details of a computer planned or virtual shoulder procedure described in FIG. 1. Method 200 relates to an anatomical shoulder arthroplasty procedure and method 300 relates to a reverse shoulder arthroplasty procedure.

First, at step 205, there is a step of importing computer generated model of selected prosthesis manufacturer, model and size for planning of an anatomic shoulder arthroplasty.

Next, at step 210, there is a step of placing the selected prosthesis on the modified patient specific model in an estimated anatomic shoulder implantation location.

Next, at step 215, there is a step of simulating motion of the patient specific model to reflect the movement of the upper extremity during an activity of daily living or a standardized clinical test.

Next, at step 220, there is a step performed during the movement of the patient specific model for activity of daily living to obtain an indication of a number of performance factors. Examples of performance factors include bone quality, forces generated, muscle performance and tension, fixation stability.

Next, at step 225, there is a step to output an overall assessment for activity of daily living or clinical test.

Step 230 is a decision step to conduct additional movements and cycles of the tested implant for another activity of daily living or a clinical test. If the answer to the decision at step 230 is "YES" then the method returns to step 215. In this case, the method loops back to testing cycles for each of the activities of daily living or clinical tests as desired by the health care provider or assessment. However, if the answer to the decision at step 230 is "NO" then the method continues to step 235.

Next, at step 235, there is a decision about whether to test another estimated implantation location or surgeon adjustment to the implant location. If the answer at 235 is "YES" then the method returns to step 210 and the prosthesis is positioned at another location. If the answer at 235 is "NO" then the method continues on to step 240.

Next, at step 240, there is a determination of whether to select a different prosthesis, manufacturer, model, size or further surgeon based input to modify location, size or other factors for the surgical procedure being evaluated. If the answer at 240 is "YES" then the process loops back to step to decision 205 for selecting a new prosthesis for testing and then method repeats for that additional prosthesis. If the answer at 240 is "NO" then the process continues to step 245.

At step 245, there is an output of all of the patient specific assessments collected during the steps 205-240. This comprehensive output includes bone quality, impingements, forces generated, muscle performance, impingement, wear and other characteristics useful for the evaluation and comparison of an implant and a proposed surgical site. Moreover, the output includes the impact on selected activity of daily living and standard clinical tests for all selected prosthesis manufacturer, models and sizes for each tested implantation site.

Figure 3:
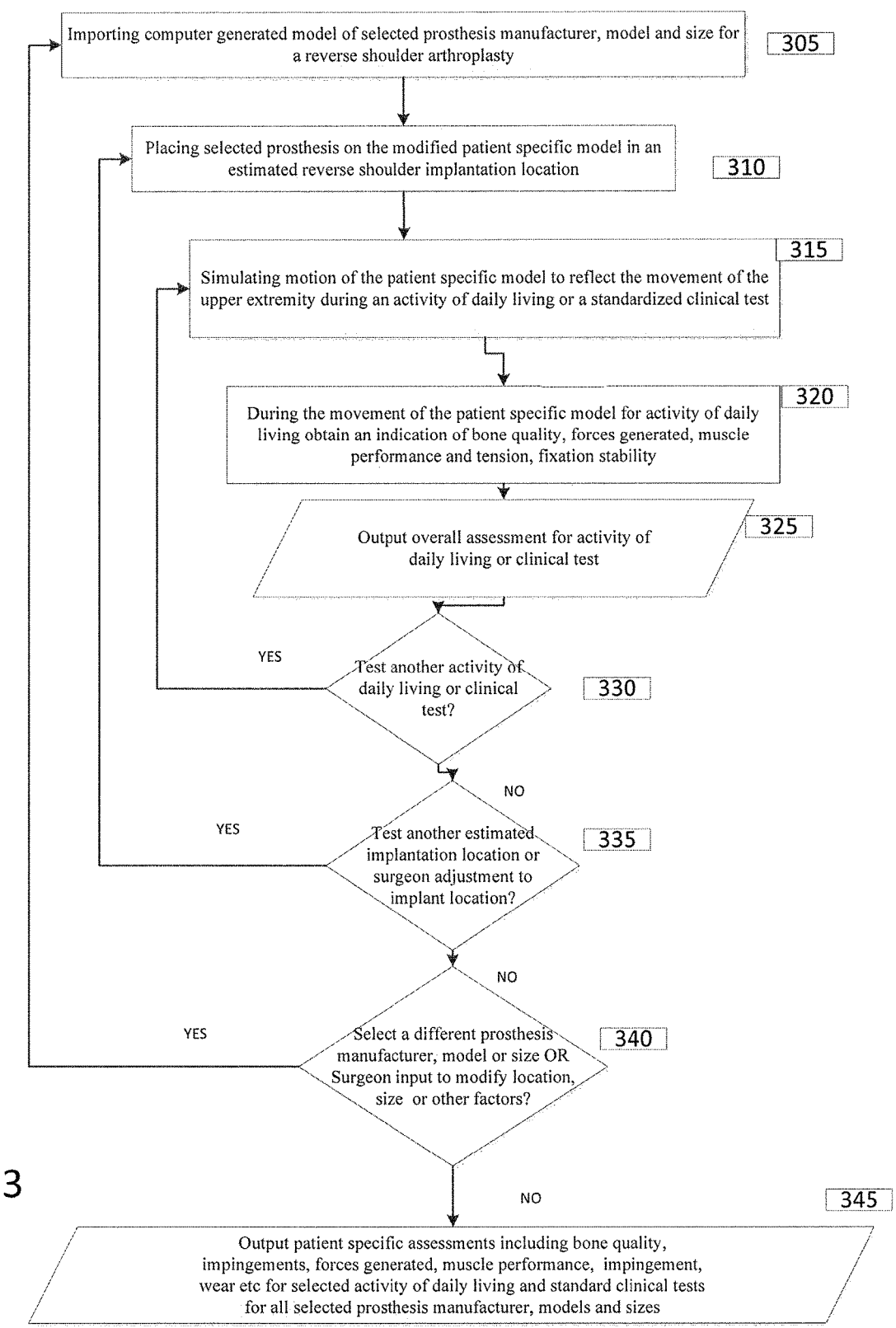
FIG. 3 is a flow chart of an exemplary computer implemented method of selecting, placing and testing an implant as part of a total joint surgery planning and evaluation system adapted for evaluation of a reverse shoulder procedure.

FIG. 3 provides exemplary steps of an illustrative method 300 related to additional details of a reverse shoulder procedure described in FIG. 1.

First, at step 305, there is a step of importing computer generated model of selected prosthesis manufacturer, model and size for planning of a reverse shoulder arthroplasty.

Next, at step 310, there is a step of placing the selected prosthesis on the modified patient specific model in an estimated reverse shoulder arthroplasty implantation location.

Next, at step 315, there is a step of simulating motion of the patient specific model to reflect the movement of the upper extremity during an activity of daily living or a standardized clinical test.

Next, at step 320, there is a step performed during the movement of the patient specific model for activity of daily living to obtain an indication of a number of performance factors. Examples of performance factors include bone quality, forces generated, muscle performance and tension, fixation stability.

Next, at step 325, there is a step to output an overall assessment for activity of daily living or clinical test.

Step 330 is a decision step to conduct additional movements and cycles of the tested implant for another activity of daily living or a clinical test. If the answer to the decision at step 330 is "YES" then the method returns to step 315. In this case, the method loops back to testing cycles for each of the activities of daily living or clinical tests as desired by the health care provider or assessment. However, if the answer to the decision at step 330 is "NO" then the method continues to step 335.

Next, at step 335, there is a decision about whether to test another estimated implantation location or surgeon adjustment to the implant location. If the answer at 335 is "YES" then the method returns to step 310 and the prosthesis is positioned at another location. If the answer at 335 is "NO" then the method continues on to step 340.

Next, at step 340, there is a determination of whether to select a different prosthesis, manufacturer, model, size or further surgeon based input to modify location, size or other factors for the surgical procedure being evaluated. If the answer at 340 is "YES" then the process loops back to step to decision 305 for selecting a new prosthesis for testing and then method repeats for that additional prosthesis. If the answer at 340 is "NO" then the process continues to step 345.

At step 345, there is an output of all of the patient specific assessments collected during the steps 305-340. This comprehensive output includes bone quality, impingements, forces generated, muscle performance, impingement, wear and other characteristics useful for the evaluation and comparison of an implant and a proposed surgical site. Moreover, the output includes the impact on selected activity of daily living and standard clinical tests for all selected prosthesis manufacturer, models and sizes for each tested implantation site.

It is to be appreciated that the use of this standardized approach to a common patient specific kinematic model provides a more complete picture of the comparison and potential benefits to a patient when selecting between anatomic or reverse shoulder arthroplasty. Still further, in some embodiments, the disclosed pre-operative planning methods can further comprise identifying a prosthetic shoulder implant for use during an anatomic shoulder or a reverse shoulder total or partial arthroplasty, including designing a patient-specific augmented humeral implant, patient specific augmented glenoid implant, and/or identifying a placement position for the prosthetic shoulder implant including anatomic or reverse procedures and including options for digital models of standard sized implants, custom implants or patient derived implants. The design and/or identification of one or more prosthetic shoulder implant components for reverse or anatomic procedures and various placement positions considered take into consideration one or more of the factors selected from the group consisting of adjustments in glenoid implant size, augmentation depth, augment position, positioning in six degrees of freedom, fixation type, fixation size, reaming depth, reaming diameter, reaming angle, and/or a combination thereof. Moreover, in additional to the above method, additional factors include steps of recommending implants and placement positions for glenoid and humeral components, with recommended adjustments in humerus stem size, length, head diameter, head height, head offset and rotation (axial). A prosthetic shoulder implant can in some embodiments comprise a glenoid implant component and a humeral implant component each adapted for use in an anatomic or a reverse shoulder arthroplasty procedure. Additional details of the above and of the various aspects of embodiments of a surgical planning system are contained in "How Computer Models Can Help Prosthesis Implantation With The Best Mobility and Minimum Impingement," by Andreas Kontaxis, Julien Berhouet, and Lawrence Gulotta; "Pre-Operative Planning and Accurate Implantation Can Increase Free Range of Motion in Reverse Shoulder Arthroplasty; Cadaveric Validation," by Andreas Kontaxis, Julien Berhouet, Daniel Choi, Xiang Chen, David Dines, Russell Warren and Lawrence Gulotta; "Humeral Version in Reverse Shoulder Arthroplasty Affects Impingement in Activities of Daily Living," by Andreas Kontaxis, Julien Berhouet, Daniel Choi, Xiang Chen, David Dines, Russell Warren and Lawrence Gulotta; "Humeral Version Affects Impingement in Reverse Shoulder Arthroplasty (RSA)," by Andreas Kontaxis, Julien Berhouet, Daniel Choi, Xiang Chen, David Dines, Russell Warren and Lawrence Gulotta; "Version Correction Compromises Remaining Bone Quality After Eccentric Reaming in B2 Glenoids," by X. Chen, A. Reddy, A. Kontaxis, D. Choi, T. Wright, D. Dines, R. Warren and L. Gulotta; "Planning Software and Patient-Specific Instruments in Shoulder Arthroplasty," by J. D. Wylie and R. Z. Tashjan; and "Dynamic Three-Dimensional Shoulder MRI During Active Motion For Investigation of Rotator Cuff Diseases," by C. Tempelaere, J. Pierrant, M. Lefevre-Colau, V. Vuillemin, C. Cuenod, U. Hansen, O. Mir, W. Skalli and T. Gregory each of which is incorporated herein by reference in its entirety for all purposes and previously identified as Appendixes A-F. Still further, additional details of the above and of the various aspects of embodiments of a surgical planning system are further described in US Patent Application Publication US 2016/0270854 and US Patent Application Publication US 2010/0125336, each of which is incorporated herein by reference in its entirety for all purposes.

FIG. 4 provides exemplary steps of an illustrative method 400 related to additional details of the method 100 described in FIG. 1 in order to compare the results obtained for the anatomical arthroplasty surgical options (FIG. 2) and the reverse shoulder arthroplasty options (FIG. 3).

First, at step 405, is obtaining the output of a patient specific assessments for all anatomic shoulder arthroplasty procedures evaluated. This output includes bone quality, tissue impingements, forces generated and how borne by the implant, muscle performance, bone impingements, wear, soft tissue balancing, and other factors assessed in the method 200. Moreover, the output includes the results for operation of the patient specific kinematic model for the selected activities of daily living and standard clinical tests (i.e., ADL) for all selected prosthesis manufacturer, models and sizes.

Next, at step 410, is obtaining the output of a patient specific assessments for all reverse shoulder arthroplasty procedures evaluated. This output includes bone quality, tissue impingements, forces generated and how borne by the implant, muscle performance, bone impingements, wear, soft tissue balancing, and other factors assessed in the method 300. Moreover, the output includes the results for operation of the patient specific kinematic model for the selected activities of daily living and standard clinical tests (i.e., ADL) for all selected prosthesis manufacturer, models and sizes.

Next, at step 415, the surgeon reviews results based on those evaluated shoulder procedures from steps 405, 410. The surgical evaluation and assessment is based on a wide array of factors, such as, for example, joint contact force and stability, muscle force, patient specific wear, kinematic factors of impingement, mechanical stability, fixation strength, soft tissue factors of comprehensive shoulder prosthesis function, standardized clinical tests, clinical assessment of patient health factors, patient prioritized activities of daily living. Still further, other characteristics and qualities may be used to evaluate suitable surgical options and prosthesis elected for this patient, as well as provide for modification of any evaluated plans.

Next, at step 420, based on the decision arrived above at step 415, the surgical planning system will output or transmit a Plan for Surgery. A Plan for Surgery includes various steps of ordering implants, obtaining any 3D printed or other patient specific implant guides, operating room and patient scheduling, and other activities to proceed with the selected and planned joint replacement surgical option. Additionally, the total joint planning system may provide optional assessment reports for use with patient consultation, information and informed consent.

In some embodiments, the methods described herein of designing and/or creating implantable components for a patient specific anatomic or reverse shoulder procedure including a glenoid implant component, a humeral implant component, shoulder surgery guide, including a glenoid implant placement guide, a humeral implant placement guide based on pre-operative planning including patient specific bone, muscle and soft tissue along with glenohumeral joint, scapula, clavicle kinematics can further comprise one or more optimization steps. Such optimization steps can comprise the identification of anatomic, surgical, procedural, range of motion, fixation, stabilization or other outcome risks based on measurements of one or more of a plurality of factors. Such factors can in some embodiments comprise indicia of glenoid face coverage, the overhang of the glenoid face and/or the bone removal on the glenoid face, the glenoid retroversion, the seating of the glenoid implant and degree the back side of the glenoid implant is supported by or touching bone, minimized penetration of the glenoid cortical wall anteriorly and/or the depth of any glenoid implant augment feature, indicia of less than about 1 mm of difference between the anatomic joint line and the new joint line with implants, indicia of minimized penetration of the glenoid cortical wall anteriorly, and/or indicia of maximized bone thickness behind the glenoid, indicia of the orientation offset between the native glenoid and implant superior/inferior axis, indicia of the superior or inferior tilt versus native glenoid, and indicia of changes in soft tissue length at extreme ranges of motion, motion during activities of daily living or in standard clinical evaluations of motion, indicia of an absence of a humeral head overhang compared to the cut, or prepared surface of the humeral bone, there is minimal difference in humeral head diameter between anatomic and implant, and indicia of the difference in humeral head height between anatomic and implant, In some embodiments, such indicia of surgical and procedural risks above or described elsewhere herein including appropriate corresponding considerations for humeral implant site preparation, surgical interaction and implantation characteristics—can be determined virtually based on images taken from a subject prior to surgery including as well the herein described patient specific total joint model including bone, muscle, tendon, soft tissue and appropriate kinematics as selected for rendered for a particular surgical situation, procedure or patient situation or episode of care.

In some aspects, there are included additional virtual model modifications to include a surgical input after a physical examination of the patient or during surgeon planning such that a tendon or a muscle group identified for the repair. Thereafter, the model can remove or diminish the contribution of the identified tendon or muscle group to maintenance of the load on the joint provided by the identified tendon or muscle group. Additionally, if a surgeon believes that the actual procedure includes a step of modifying a tendon or muscle group such as for example using the deltoid to stretch up and attach to the joint then that expected actual modification to deltoid attachment may be factored into the overall model. In this instance, the planning model indicates where a physician specific indication of surgical preference can be included into the model before the model is cycled to assess the various factors of a selected surgical procedure. Such a modification would allow a surgeon to experiment with long-term fixation and stabilization based on decisions made about soft tissue management and the use of a specific prosthesis or long-term stability, fixation and wear. In addition, a surgeon may indicate as a factor included in the system output a level of prior experience in the use of, confidence factor in or other subjective selection criteria or factors related to a specific manufacturer or a specific model of prosthesis under consideration. Additionally, a surgeon may indicate a subjective evaluation that design qualities or engineering features of a specific manufacturer prosthesis or model would be particularly suited to a patient procedure under evaluation.

In still another aspect, the virtual model of planned patient intervention optionally provides that one or more muscles, ligaments, tendons can be dropped or manipulated by the surgeon with respect to the model in order to predict outcomes to fixation, stabilization and longevity depending upon projected surgical technique and management of soft tissue in the joint. Soft tissue management in the planning module allows the surgeon to indicate whether or not a particular muscle is sufficiently strong, flexible, or robust enough to aid in stabilization of the joint post-surgery. Moreover, if a surgeon determines that one or more pre-identified or defined muscle, tendon or ligament will not be reconnected or will not aid in the loadbearing considerations factored by the model then the surgeon can elect to remove that ligament muscle or tendon from the modeling considerations for assessing and characterizing selected implants and procedures.

In one specific example, a patient may not have a rotator cuff so the associated tendon may be removed from the model or discounted using weighting factors from the model as it generates the various outcomes produced by the activities for daily living.

FIG. 5 provides exemplary steps of an illustrative method 500 related to additional details of evaluation, ranking or scoring the outcomes provided by the assessment and planning steps of method 100 described in FIG. 1.

First, at step 505, there is a step of obtaining a summary output including ranking, scoring, comparisons, graphics or other suitable outputs to aid in the evaluation of the performance and characteristics for all selected or evaluated implants, including various surgical locations or procedures.

Next, a step 510, there is a step of conducting a patient-surgeon evaluation, assessment and consent for perform the surgical procedure based on the modeled and evaluated procedure. Thereafter, at step 515, there is the selection of a patient specific planned implant, location and procedure.

Next, at step 520 is the step to obtain or order materials related to the selected patient specific procedure including patient specific guides, implants, and components or planning from selected vendor or implant manufacturer.

Finally, at step 525, is the step of performing the selected patient specific planned surgery.

In one specific embodiment, an output of the system is a scorecard of the various characteristics or factors that result from testing the prosthesis size and location as predicted against the activities of daily life for that specific patient. A standard scorecard or info graphic of key characteristics may be useful for the surgeon to compare different prosthesis sizes or implant locations as well as advising the patient for informed consent or to indicate the impact on activities of daily living depending upon surgical decisions made. In one aspect, a patient and surgeon may discuss prosthesis election options based upon optimization of prioritized activities of daily life and informed consent on prosthesis selection and implant location based upon elected impact on specific activities of daily life. For example a patient may choose to optimize the surgical the projected surgical outcome in order to restore motion so that the patient may continue to play golf. Other motion restrictions may be implied within the election to optimize for golfing activities over other motion activities for daily living.

Figure 6:
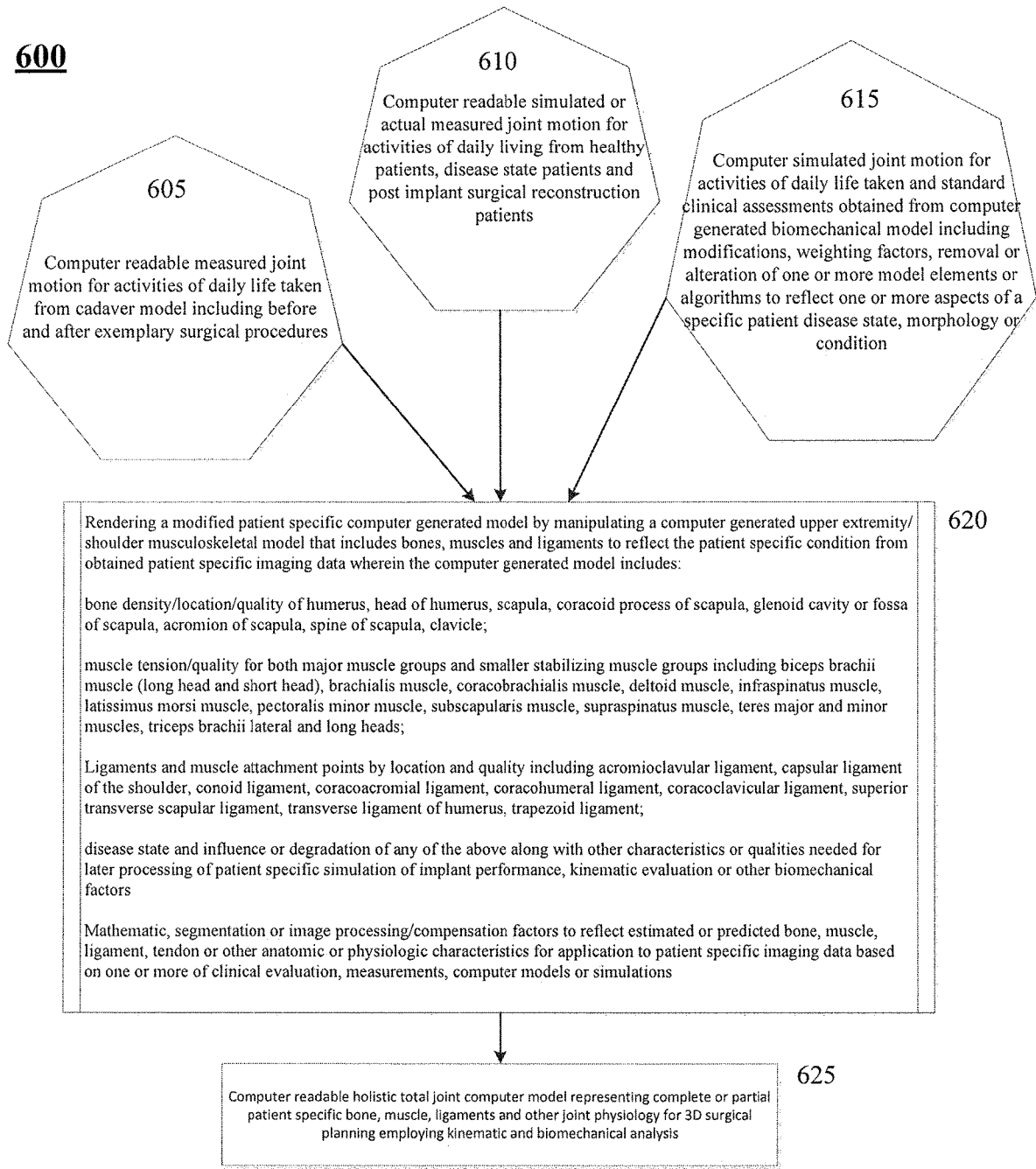
FIG. 6 is a flow chart of an exemplary computer implemented method of adapting a joint specific anatomic and kinematic model to reflect the condition of a specific patient who is undergoing evaluation and assessment of planning for a partial or total joint surgery as in FIGS. 1, 2 and 3.

FIG. 6 provides additional types of inputs 605, 610 and 615 that may be used in additional total joint planning model 620 to produce alternative patient specific models 625 for use in the various total joint surgical assessment and planning methods described herein. While 620 relates specifically to the anatomy of the shoulder, this step would be modified according to the specific anatomical details of the joint under assessment.

Step 605 indicates a source of joint motion for adaptation of the patient specific joint model. Examples include computer readable measured joint motion for activities of daily life taken from cadaver model including before and after exemplary surgical procedures.

Step 610 indicates another source of joint motion information for adaptation of the patient specific joint model. Examples include computer readable simulated or actual measured joint motion for activities of daily living from healthy patients, disease state patients and post implant surgical reconstruction patients.

Step 615 indicates another source of joint motion information for adaptation of the patient specific joint model. Examples include computer simulated joint motion for activities of daily life taken and standard clinical assessments obtained from computer generated biomechanical model including modifications, weighting factors, removal or alteration of one or more model elements or algorithms to reflect one or more aspects of a specific patient disease state, morphology or condition.

Step 620 relates to the step of rendering a modified patient specific computer generated model by manipulating a computer generated model of a total joint being evaluated by the total joint surgical planning system described herein. In the specific example of step 620 for a shoulder arthroplasty, the computer generated or virtual model would include an upper extremity/shoulder musculoskeletal model that includes bones, muscles and ligaments to reflect the patient specific condition from obtained patient specific imaging data. By way of additional and illustrative examples, the computer generated model includes one or more or a combination of:

(a) bone density/location/quality of humerus, head of humerus, scapula, coracoid process of scapula, glenoid cavity or fossa of scapula, acromion of scapula, spine of scapula, clavicle;

(b) muscle tension/quality for both major muscle groups and smaller stabilizing muscle groups including biceps brachii muscle (long head and short head), brachialis muscle, coracobrachialis muscle, deltoid muscle, infraspinatus muscle, latissimus morsi muscle, pectoralis minor muscle, subscapularis muscle, supraspinatus muscle, teres major and minor muscles, triceps brachii lateral and long heads;

(c) ligaments and muscle attachment points by location and quality including acromioclavular ligament, capsular ligament of the shoulder, conoid ligament, coracoacromial ligament, coracohumeral ligament, coracoclavicular ligament, superior transverse scapular ligament, transverse ligament of humerus, trapezoid ligament;

(d) disease state and influence or degradation of any of the above along with other characteristics or qualities needed for later processing of patient specific simulation of implant performance, kinematic evaluation or other biomechanical factors; and (e) mathematic, segmentation or image processing/compensation factors to reflect estimated or predicted bone, muscle, ligament, tendon or other anatomic or physiologic characteristics for application to patient specific imaging data based on one or more of clinical evaluation, measurements, computer models or simulations.

Finally, at step 625, based on the inputs from steps 605, 610, 615 and 620, a computer readable holistic total joint computer model is rendered suitable for the various manipulation and surgical planning procedures and biomechanical simulations described herein. In one aspect, this computer readable model representing a complete or a partial patient specific bone, muscle, ligaments and other joint physiology for 3D surgical planning employing kinematic and biomechanical analysis. In some aspects, the majority of the modeling information reflects data from the patient specifically.

Activities of daily living include any of a wide array of motions of the extremities for personal health, hygiene or occupational activities. In still another additional aspect, activities of daily living could also include sports related or specific activity related motions such as golf, tennis, or other specific activities that involve the specific motion of the extremities. These may be selected and prioritized as part of the inputs into the model for a particular patient. As part of informed consent, the patient and surgeon may discuss the various options as indicated in the model outputs as to the impact of selecting particular activities of daily life and motion of the extremities that may have a detrimental impact on one or more qualities of long-term outcome for the patient and surgically modified joint such as fixation, stabilization or range of motion.

Factors for evaluation of an implant include range of motion of the joint, stability of the joint and fixation.

Range of motion of the joint is limited within the software model to actual range of motion as indicated by the soft tissue limitations of the actual patient anatomy including factors such as the removal of muscle, tendon or ligament from the surgical plan, as elected by the surgeon, as part of the surgical planning process. Range of motion analysis also includes output for potential risk of impingement, notching or loosening by misalignment of the joint during certain activities for daily living.

The stability of the joint relates to the risk of the location of the joint. In many cases stability is increased at the expense of range of motion. Compromises such as these between factors may be reflected in the planning system outputs.

Fixation relates to how loading effects on the joint caused by activities of daily living are likely to loosen or dislodge the prosthesis. In particular in a reverse shoulder arthroplasty the loading forces on the joint are nearly the opposite of the loading that occurs in an anatomical shoulder arthroplasty. As a result the manner with which the joint is moving shifts the way that load forces are transferred into the prosthesis, mount, screws and associated bone.

More specifically as related to fixation, in a anatomic shoulder arthroplasty, muscles are present and are in compression about the joint. Additionally, the rotator cuff is present and may contribute to supporting part of the loading on the prosthetic joint thereby aiding in the ability and mitigating some fixation affects caused by activities of daily living. In contrast, in a reverse shoulder arthroplasty rotator cuff is gone or only a small amount of tissue remains. As a result the stabilizing effect and load sharing affect provided by the rotator cuff is diminished severely. Moreover, because the reverse arthroplasty loads the joint in a different way than is natural to the joint, previous activities of daily living may actually contribute to increased force loads and share forces instead of compressive loads being present in the joint. In some cases screws and base plates may loosen as a result of shear forces present in the reverse arthroplasty procedure. Importantly, the model described herein is able to provide the ability to adjust loading and positioning in the reverse arthroplasty procedure in order to adjust and minimize shear loading effects on the prosthetic joint. In other words, the model may account for load changes in the joint based on the prosthesis implant location and anchor conditions. As a result, prosthesis, bone and soft tissue model provides for more precise load calculations and dynamic load scenarios in the prosthetic joint whereby the variation of loading scenarios can be used to drive prosthetic position and prosthetic size selection decisions.

In some aspects, the model described herein may be used to further elaborate the consequences of typical surgical decisions in various arthroplasty procedures.

Typically, in a reverse arthroplasty procedure, the prosthesis is implanted in a position as low as possible. In some patients this typical practice may lead to notching in circumstances above average. The comprehensive bone and soft tissue model described herein will help identify whether and to what degree a low implant position adversely affects fixation, stability or range of motion on a patient specific basis.

In some procedures, the deltoid may be stretched and reattached to the joint in a different location than is the anatomic attachment point for the deltoid. The model will allow the surgeon to indicate the planned attachment point for the deltoid. The model will then account for the loading effect on the joint of the use of the deltoid as surgically attached to the prosthetic joint. Because the deltoid is helping to carry part of the loadbearing of the prosthetic joint, implant positions and implant selection may lead to different choices. Providing surgical input or soft tissue manipulation is one of the advantages of the model and scenario generator of the surgical planning system.

To further elaborate on planning in a reverse shoulder prosthesis, surgical modifications and recommendations may also be provided where a surgeon may evaluate additional removal or resection at different angles of the humeral head in order to result in different prosthetic locations. Aspects of the model described herein include the total joint factors or both sides of the joint. This further underscores an advantage of the modeling indications and selections described herein will be different for the anatomic and for the reverse procedures. In this way, the model may advantageously recommend a greater or different resection of bone to avoid further cutting into the humerus.

Additionally, the model may include characteristics of the soft tissue such as muscle tension, muscle attachment point, ligament health, tendon health as well as various attachment points of soft tissue and relationship of soft tissue to the prosthetic location as well as contribution to load sharing of the joint forces generated during activities of daily living.

The model may be used to generate outputs that are used to manage patient expectations about the impact or difficulty on activities of daily living based on the selection of a particular prosthesis or surgical election such as the consequences of doing an anatomic arthroplasty procedure or a reverse arthroplasty procedure.

The software includes tools for the surgeon to micro adapt or make small adjustments or modifications to selected surgical implant locations and recommendations so that the specific implant location may be driven by specific surgeon inputs.

Advantageously, the surgical planning system described herein includes a total joint patient selective model that is interactive and inclusive for the bones, the soft tissue and the surgical impact to both of a particular prosthesis selection (vendor, model, size) as well as surgical procedure election between an anatomic shoulder arthroplasty and a reverse shoulder arthroplasty. For each of the selections above the prosthetic joint is articulated through a number of motion simulations that mimic the activities of daily living as specified by consultation with the physician and the surgeon. A patient or surgeon may elect to weigh heavily particular activities of daily living to ensure that prosthesis selection and implant location are optimized for performance of particular activities. In this way the patient and surgeon may decide together on particular prosthesis or implant locations based on optimization of activities for daily living.

Figure 7:
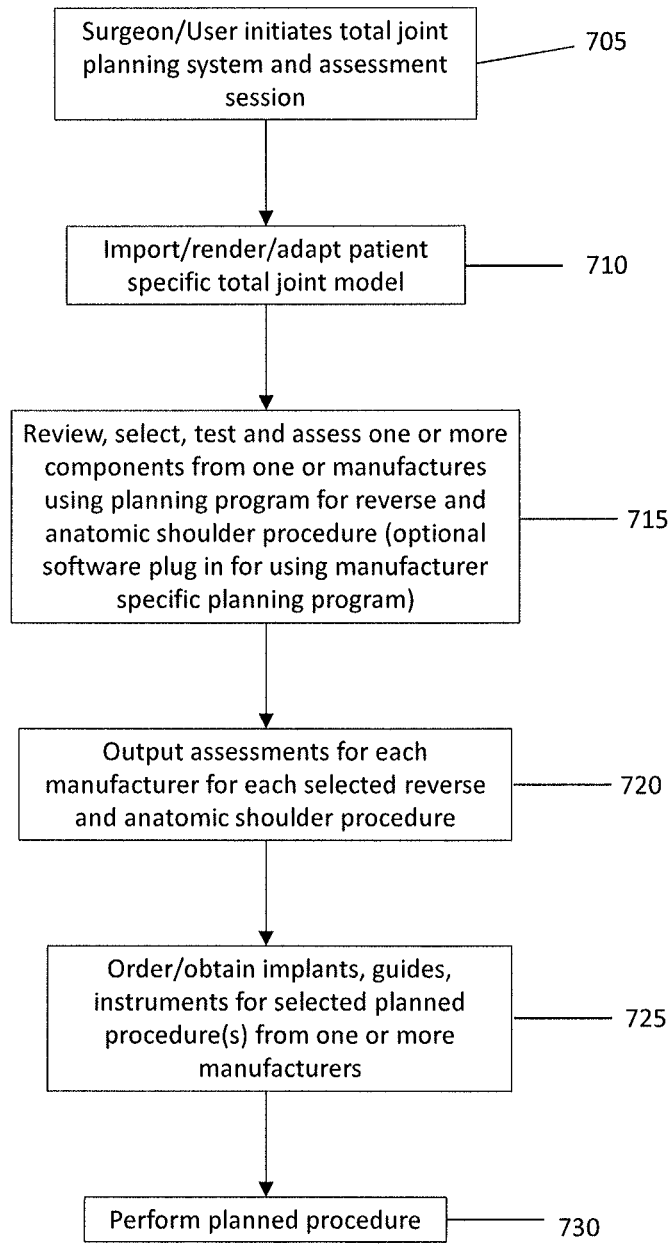
FIG. 7 is a flow chart of an exemplary computer implemented method of importing, selecting, placing and testing an implant as well as performing a total or partial joint surgery.

FIG. 7 illustrates an exemplary total joint surgical planning method 700 according to aspects of the inventive techniques described herein.

First, at step 705 the surgeon/user initiates a session with a total joint planning and assessment system.

Next, at step 710, there is a step of importing into the planning and assessment system a patient specific total joint model. The imported patient specific model is rendered and adapted as needed to represent the conditions and characteristics of the patient at the intended surgical site.

Next, at step 715 there is a step of reviewing, selecting, testing, and assessing one or more components from one or more manufacturers using the surgical planning program. In one aspect, the total joint surgical planning and evaluation program may provide assessment and testing for anatomical shoulder arthroplasty and reverse shoulder arthroplasty procedures. Optionally, the total joint surgical planning and evaluation program may include plug-ins or porting capabilities to use a manufacturer specific planning or simulation software program.

Next, at step 720 there is the step of outputting the assessments for each manufacturer for each selected surgical location and procedure. In one aspect, each anatomic shoulder procedure and each reverse shoulder procedure is included in a summary comparison having common elements as discussed herein to ensure that there is a common baseline for evaluation.

Next, at step 725 there is a step of ordering or obtaining the implants, guides, instruments for the selected and planned procedures from the manufacturer or manufacturers selected based on the prior assessment steps. This step includes patient specific instruments or implants as well as those patient specific implants or surgical guides that are obtained using an additive manufacturing technique, for example a 3-D printing technique. In some embodiments, the patient specific imaging information or modified information using in the methods described herein are used to design components produced during the additive manufacturing process in support of the patient specific joint surgery described herein.

Next, at step 730 there is the step of performing the planned procedure as determined based on the method of steps 705-725.

Figure 8A:
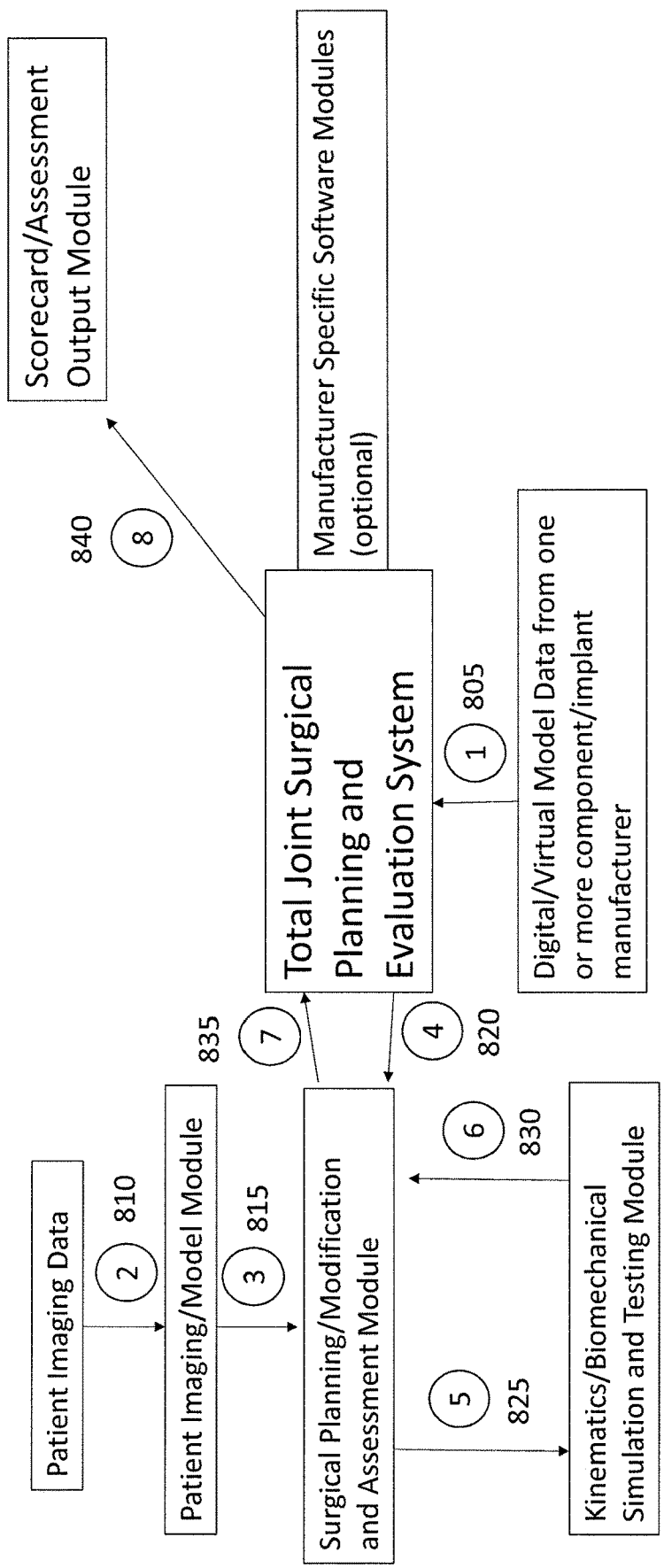
FIG. 8A is a flow chart of an exemplary computer implemented method of utilizing a total joint surgical planning and evaluation system.

An exemplary work flow for the use of a total joint surgical planning and evaluation system 800 is provided in FIG. 8A. The work flow 800 follows steps 1-8. The first step is the creation or access to a digital/virtual model library containing electronic models of various components, implants, tools, guides, kits and the like for use in the system. Next, the second step, is to collect patient imaging data (810). Thereafter, the patient imaging data is provided to the patient imaging/model module (815). Next, the patient imaging data is combined with implant data (820) in the surgical planning/modification and assessment module. After performing a virtual surgery to place the selected implant into the patient specific kinematic model, the model is manipulated to provide a variety of simulations and testing corresponding to activities of daily living and other clinical testing as desired. The next step 835 is to report all results of the assessment module to the total joint surgical planning and evaluation system. An output of all testing simulations performed is provided as a scorecard or assessment tool (step 840). An example output 845 of the evaluation system is provided in FIG. 8C.

Exemplary manufacturers and suppliers of orthopedic implants, tools, computer aided planning systems as well as patient specific guides, instruments and components are listed below including representative patent applications that further detail the offerings of that particular manufacturer. As shown in FIG. 8A in the overall system 800, as well as in the exemplary data set 805 (see FIG. 8B), one or more component manufactures may elect to be included (as in actively provide digital model data suited for use in the total joint surgical planning system) in which case the data flows from the manufacturer into the system for use—based on surgeon selection—during a selected procedure planning or evaluation session. Optionally, one or more or all of the components from a manufacturer may be scanned, rendered or modeled in an appropriate form and with enough detail to permit use for planning and evaluation using the systems described herein. In one aspect, a manufacturer with components listed may also provide direct order or a link for use with the planning system such than once the selected plan is approved, the surgeon or designated representative may order the components, implants, guides, Patient Specific Instruments (PSI) or other tools or accessories recommended by or provide by the manufacturer. In an additional further aspect, the planning and assessment is linked to the procurement system of the surgeon or provider system to permit further coordination of scheduling whereby the surgical planning date may be compared to any lead time for the preparation, manufacture or delivery of any selected manufacturing component. Optionally, when planning, a manufacturer may indicate availability of or lead time for delivery of any planned item in order to further aid the surgeon or provider or planner for patient scheduling of the evaluated and selected procedure. As is illustrated in FIGS. 8A, 8B and 8C, the output of the planning and evaluation planning system enables a user to compare side by side the various assessment criteria for a specific patient under the prioritized selection criteria for that patient. In this way, a surgeon may have increased confidence in the comparison of different procedures as well as implants—independent of manufacturer—in order to asses—on a patient specific basis whether an anatomic or reverse shoulder procedure would best provide the desired outcome based on the factors discussed herein.

In many cases, additional technical details and names of components to be rendered in digital form for use in the surgical planning and assessment system are described in one or more of the following patent application. Each one of the patents and patent applications listed below is incorporated herein by reference. Moreover, whether provided directly by the manufacturer or obtained by rendering, scanning or other imaging techniques, digital models of the components, implants, guides, Patient Specific Instruments, or other instruments described in patents, patent applications or in the Appendices are included as representative of the digital/virtual model data that is available for use by the total joint surgical planning and evaluation system (FIG. 8A). Still further, in some embodiments of the inventive total joint planning system, a user may select a vendor or manufacturer and obtain digital models of one or more vendor specific components to be used in the assessment of a selected reverse or anatomic procedure as described herein. In one aspect, the total joint virtual planning system described herein includes appropriately configured communication links either to stored or remote data provided by the selected manufacturer for use in the comparison, assessment and output functions described herein. The system may draw from a local data storage with recent, confirmed release and available components or, optionally, a specific user may have access to one or more experimental or developmental or evaluation components for use in the surgical planning system described herein. A representative table of manufacturer data compiled for this purpose is represented in FIG. 8B and table 805.

Advantageously, the availability of component selection from a variety of vendors enables a surgeon to consider within the same virtual patient model, as appropriate, different products for standard, custom, sized, or patient specific implants, components, guides, instruments and the like. One manufacturer is Arthrex. Another manufacturer is Smith and Nephew with additional details available in US Patent Application Publication US 2016/0120555, US 2012/0109226 and US 2014/0081342 as well as US Provisional Patent Application No. 61/373,092. Another manufacturer is DePuy with additional details available in US 20130066321. Another company is Conformis US2015/0223941 and US 2015/0223941 and PCT/US13/56841. Another company is BioMet Publ US 2014/0107654, application Ser. No. 13/653,893 and U.S. Pat. No. 9,301,812, US 2013/0110470 including the Signature Personalized Patient Care System—Glenoid Guide System US 2013/0110116; US2014/0107715 and including the "Comprehensive Total Shoulder System featuring comprehensive access glenoid instrumentation" and including the Custom Orthopaedic Solutions, Inc, a Subsidiary of Cleveland Clinic. Glenoid Intelligent Reusable Instrument System, US20120143267; US 2012/0109137; DJO or Don Joy including the Match Point System, SurgiCase system and Materialize WO2013/0608851; PCT EP 2012 071272 (WO2013060851A1); US 2014-0236158; US 2016/0192951; US 2011/0130795; Zimmer PSI Shoulder, PSI Glenoid and PSI Reverse Shoulder. A still additional manufacturer is Wright Medical and including Tornier BluePrint 3D Planning+PSI and the Aequalis PerFORM Glenoid System; US 2007/0250174, and WO 2015/071757 (Tornier).

Including digital models of components from manufactures listed below or digital models of the products listed below or of all selected products having regulatory approval. The digital models of the components utilized in the system may be obtained from the manufacturer or obtained using a conventional scanning and rendering process using a physical sample. In some embodiments, the digital/virtual model data includes data of products from manufactures as well as digital models of FDA approved devices, including those used in the exemplary table listings below:

CAS PSI Shoulder, Zimmer CAS (K131129)
SurgiCase Orthopaedics, SurgiCase Connect, SurgiCase Guides Materialise N.V. (K112389)
Signature Personalized Patient Care System—Glenoid Guide System. Biomet Manufacturing Corp (K130126)
Match Point System, Match Point System Guide, SurgiCase Connect, Materialise N.V. (KA131559).
Acqualis PerFORM glenoid System, TORNIER SAS (K111902)
OsiriX M D, Pixmeo, SARL (K101342)

| Main features or system characteristics | BLUEPRINT ™ Patient Specific Instrumentation | CAS PSI Shoulder Guide (K131129) | SurgiCase Guides (K112389) | Signature Personalized Patient Care System - Glenoid Guide System (K130126) | Match Point System Guide (K131559) | Aequalis PerFORM glenoid System (K111902) | OsiriX MD (K101342) |
|---|---|---|---|---|---|---|---|
| Material | Polyamide 2200 | Polyamide | Polyamide 2200 | Plastic | Polyamide 2200 | UHMWPE + CoCr | NA |
| Standard | USP Class VI compatible | Unknown | USP Class VI compatible | Unknown | USP Class VI compatible | ISO 5834-2 ISO 5832-7 | NA |
| Product Code | KWS | KWS, PBF | PBF | KWS, KWT. PAO-. and MBF | KWS | KWS | LLZ |
| Surgical procedure | Total anatomic shoulder arthroplasty | Reversed shoulder arthroplasty | Upper extremities | Total and reverse shoulder arthroplasty | Total and reverse shoulder arthroplasty | Anatomic shoulder arthroplasty | Mammography |
| Single-use | Yes | Yes | Yes | Yes | Yes | Yes | NA |
| Sterile | No | No | No | No | No | Yes | NA |
| Manufacturer | Tornier SAS | Zimmer | Materialise N.V. | Biomet | Materialise N.V. | Tornier SAS | Pixmco, SARL |

In still other aspects, a score card or evaluation or assessment may include one or more factors as indicated herein. The score card is similar to an output from the result of the use of the Total Joint Surgical Planning and Evaluation System to assess a proposed surgical procedure for a patient. The output is designed to provide outputs that are useful in the assessment of similar or standard tests as described herein on a patient specific model. In this way the assessment provides information that is common across all procedures or prosthetics under evaluation. In one exemplary embodiment, the score card appears as in the output 840 in FIG. 8A and shown in FIG. 8C in table 845. One or more of the manufacturer specific surgical planning systems may also be included as a module, pop up or embedded operation for placement of the manufacturer digital models into the patient specific total joint model and as used in the total joint surgical planning and evaluation system.

of a glenoid component and the model will operate to determine whether additional resection or modification of the resection to the humeral bone would benefit or enhance any of the factors of improved joint outcome-fixation, stability and range of motion. These and similar surgical modifications as attempted in the planning software are all carried with the data set for the recommendations and outputs of other modules, as in steps 130, 135 and 140 of method 100 (FIG. 1), as well as to modifications, for example, to the methods 200, 300, 500, 700, and 800.

In some embodiments, a method of creating a reverse or anatomic shoulder surgery guide comprises utilizing one or more of the above steps, analyses, optimizations and recommendations to create a patient specific shoulder surgery guide. Guide creation can comprise automated design and creation of a three dimensional model of a glenoid and/or humeral guide reflecting one or more optimized parameters

| Validation and/or Verification Method | Acceptance Criteria description | Verification and Validation Results |
|---|---|---|
| Seating Validation Test | The seating offset between reference method and the software calculation should be compliant | Acceptable |
| Reaming validation Test | The Reaming offset between reference method and the software calculation should be compliant | Acceptable |
| Orientation and Direction angles Validation Test | The orientation angle offset and the Humeral Head Subluxation direction offset between reference method and the software calculation should be compliant | Acceptable |
| Glenoid Version and Inclination angle validation test | The version angle offset between reference method and the software calculation should be compliant A concordance correlation coefficient ρ between the reference method and the software calculation of the inclination should be compliant | Acceptable |
| Humeral Head subluxation and direction measure | The Humeral Subluxation offset and the Humeral Head Subluxation direction offset between reference method and the software calculation should be compliant | Acceptable |
| Patient Specific Guiding Wire test | Version angle error, inclination angle error and entry point error should be compliant | Acceptable |
| Segmentation Accuracy Test | Mean Distance Error in the surgical zone between 3D reconstruction and the reference reconstruction should be compliant | Acceptable |
| Clinical Case Series | Pre-operative Plan compared to post-operative implant position | Acceptable |

Any of the above described may be utilized in one or more of the steps of the methods and systems detailed in FIGS. 1-9C.

In still other advantageous features, the surgical planning model includes the ability to account for rotation of the glenoid component and the impact to the humeral side of the joint. For example, a surgeon may elect a particular rotation determined during pre-operative planning based on the method steps described herein.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

Also provided herein are methods, systems and devices for creation of a glenoid implant or glenoid prosthesis based on pre-operative planning which takes into consideration a plurality of factors and assessments. In some embodiments, the creation of a glenoid implant based on pre-operative planning can comprise one or more of the following steps, the combination and order of which can vary: aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting the medialization of the glenoid implant by assessing the volumetric amount of bone needed to be removed by reaming, or the minimum total distance of reaming necessary, in order to optimize the bone to implant interface; analyzing the fixation support in the absence of central pegs that penetrate a vault medially; analyzing the joint line, comprising comparing an original joint line and a new joint line, wherein the new joint line is substantially similar to the original joint line; measuring and matching widths of the glenoid implant and the glenoid bone after reaming and aligning inferior/superior axes of the glenoid implant and bone; assessing and adjusting as needed a thickness/height of the glenoid implant; assessing and adjusting as needed a depth of a glenoid fossa; assessing and adjusting as needed a thickness of a graft; determining a diameter of a humeral head; determining a height of the humeral head; determining a size of humeral bone implant; and/or determining a best fit size of implant from a range of manufacturer designs and sizes, wherein the range of sizes is selected from the group consisting of length of stem, size of humeral stem, diameter of stem, size diameter of head, height of head, and offset of the center spherical head compared to the center of the face of the humeral stem.

In some aspects, the planning methods and analysis steps disclosed herein can be done pre-operatively. That is, they can be done prior to surgery in a virtual or software-based environment. Such virtual simulations can in some embodiments be based on images or scans taken from a subject prior to surgery. Currently available and future imaging techniques, e.g. computed tomography (CT), x-ray imaging, positron emission tomography (PET), ultrasound, etc., can be used to capture images and data to be used in simulation-based analysis and planning to identify suitable prosthetic implants and/or design surgery guides. In some embodiments, Digital Imaging and Communications in Medicine (DICOM), which is known as a standard for handling, storing, printing, and transmitting information in medical imaging, can be utilized. DICOM can in some embodiments provide for the integration of scanners, servers, workstations, printers, and network hardware from multiple manufacturers into a picture archiving and communication system (PACS). Application areas for DICOM Images are CT, MRI, PET, and Ultrasound, among others. By using images captured from a subject or patient to be treated, the analysis and results can be specific to the subject or patient and can take into consideration the particularities of that subject's condition. Any of the above imaging modalities, techniques or systems may be used as part of the patient imaging capture, rendering or modification as described above, for example, in steps 105, 110 in method 100, method 200, 400, 600, 710, 810, 815, 900, 915, and 920 or as otherwise needed for the operation of the specific implementation of the total joint surgical planning and evaluation system.

In some aspects, when the anatomic or reverse procedure pre-operative planning is conducted, the actual morphologic form of the involved native bones of a patient to be treated is considered and imaged. In order for the fit and configuration of the selected implants to be correct, the form of the involved bones as found on a CT scan, for example, are used to create a "reverse image" that is incorporated in the implant design. Likewise, in order for the positioning of a specific placement guide to be correct, the form of the involved bone as found on a CT scan, for example, is used to create a "reverse image" that is incorporated in the guide design for the involved bone or portion thereof.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As such, in some embodiments the disclosed pre-operative planning methods can further comprise providing a computer readable medium having stored thereon executable instructions that when executed by the processor of a computer control the computer to perform one or more of the planning method and/or analysis steps. For example, in some embodiments computer readable medium can have stored thereon executable instructions that when executed by the processor of a computer can control the computer to generate a virtual 3D model of an augmented or patient-specific glenoid implant and/or a glenoid guide device, e.g. a glenoid placement guide, reflecting one or more optimized parameters determined during pre-operative planning. Additionally, in some aspects, computer readable medium can have stored thereon executable instructions that when executed by the processor of a computer control the computer to control a 3D printing device in communication with the computer, whereby the 3D printing device can print a patient-specific, i.e. customized, augmented glenoid implant and/or a glenoid guide device or humeral guide device for use in shoulder replacement surgery in a patient for which pre-operative planning method steps were conducted.

In still further aspects, the planning system embodiments described herein include additional interfacing capabilities to allow multiple different component manufactures to provide, update or make available legacy, new development, experimental or regulatory approved implants for human use according to the various planning and evaluation methods described herein. In a similar way, the planning system described herein may also provide plugins or sockets and modifications to UI and GUI interfaces thereby permitting communication to manufacturer specific surgical planning systems as well as related patient specific instruments and planning guides. In this way, a surgeon using the total joint multiple manufacturer system would have wide freedom to more readily compare and assess available implants and surgical guides for a specific patient surgical situation for a more complete consideration of the various patient specific implications for an anatomic or a reverse shoulder procedure. Exemplary commercially available implant manufactures and associated manufacturer specific surgical planning systems are described in "Planning Software and Patient-Specific Instruments in Shoulder Arthroplasty," by J. D. Wylie and R. Z. Tashjan; referred to previously as Appendix E, incorporated herein by reference for all purposes.

Further, in some aspects of the disclosed methods, systems and devices, a computer readable medium can be provided having stored thereon executable instructions that when executed by a processor of a computer can control the computer to generate a virtual 3D model of a patient-specific, i.e. customized, augmented glenoid implant and/or a glenoid implant device or placement guide device reflecting one or more optimized parameters determined during pre-operative planning. Thus, in some embodiments a computer readable medium is provided, wherein the computer readable medium has stored thereon executable instructions that when executed by the processor of a computer control the computer to perform one or more of the planning method and/or analysis steps as disclosed herein.

It should be noted that the computers, computing devices, hardware and/or functionality described herein may constitute a special purpose test device. Further, computers, computing devices, hardware and/or functionality described herein can improve the technological field of pre-operative planning for shoulder surgery and can improve generation of virtual modeling systems.

The subject matter described herein for generating 3D models of glenoid and/or humeral implant devices, and/or for modeling and virtually simulating pre-operative reverse and anatomic shoulder surgery analysis improves the likelihood of a positive outcome from shoulder surgery. It should also be noted that a computing platform, computer, computing device, and/or hardware that implements the subject matter described herein may comprise a special purpose computing device usable to generate 3D models of glenoid and/or humeral implant devices, and/or for modeling and virtually simulating pre-operative reverse and anatomic shoulder surgery analysis.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments a computer readable medium is provided, having stored thereon executable instructions that when executed by the processor of a computer control the computer to perform steps comprising generating a virtual three dimensional model of a glenoid and/or humeral guide reflecting one or more optimized parameters determined during pre-operative planning based on the above method steps. In some embodiments, a computer readable medium is provided, having stored thereon executable instructions that when executed by the processor of a computer control a 3D printing device in communication with the computer, whereby the 3D printing device prints a glenoid and/or humeral guide, or placement guide, for use in anatomic or reverse shoulder replacement surgery in a patient for which the optimization analysis was conducted.

In some embodiments, provided herein are pre-operative planning and shoulder surgery kits for each selected reverse and anatomic procedure. Such kits can in some aspects comprise a set of instructions for performing pre-operative analysis steps as disclosed herein, and one or more guides, glenoid prosthetic devices and/or humeral prosthetic devices. In some embodiments, a kit can comprise a 3-D printing device for producing a guide and/or one or more glenoid and/or humeral prosthetic devices. In some embodiments, a kit can comprise a computer-readable medium for use in conducting the pre-operative planning, and designing a guide, glenoid implant and/or humeral implant based on input parameters gathered during the pre-operative planning. In some embodiments, the devices are customizable and/or modular in design such that the prosthetic device can be optimized for the patient based on the pre-operative planning analysis. In some aspects, a kit can comprise a range of glenoid implants having augmented back sides where the augmentation is selectable in terms of the augmentation size, shape, and position, both in the superior/inferior and posterior/anterior position. In some embodiments, a kit comprising a range of glenoid implants having augmented back is provided where the augmentation is selectable in terms of its size, shape, and position, where the position is defined by an angular and a radial position.

In some embodiments, methods of treating a patient, and/or surgical methods, are provided wherein one or more of the disclosed methods of analysis and optimization are performed on a patient in need of shoulder or other joint surgery. In some embodiments, methods of treating a patient are provided wherein a disclosed method of analysis and optimization is performed, an optimized guide is designed and created, and one or more glenoid and/or humeral implants are designed, created, and/or selected. In some embodiments, a method of treating a patient can comprise utilizing the pre-operative planning to design and optimize a guide and one or more glenoid and/or humeral implants, and the use of the guide to surgically implant the one or more glenoid and/or humeral prosthetic devices according to a selected anatomic or reverse shoulder procedure.

The presently disclosed subject matter provides methods, systems and devices for virtual pre-operatively planned humeral and glenoid implants and prosthetic devices for anatomic or reverse shoulder surgeries while also accounting for range of motion desired for activities of daily living and/or standard clinical assessments of range of motion. The presently disclosed subject matter also provides for planned methods including patient specific instruments for the surgical preparation and implantation of humeral and glenoid implants in patients undergoing reverse or anatomic shoulder surgery.

In some embodiments, the methods described herein of designing and/or creating implantable components for a patient specific anatomic or reverse shoulder procedure including a glenoid implant component, a humeral implant component, shoulder surgery guide, including a glenoid implant placement guide, a humeral implant placement guide based on pre-operative planning including patient specific bone, muscle and soft tissue along with glenohumeral joint, scapula, clavicle kinematics can further comprise one or more optimization steps. Such optimization steps can comprise the identification of anatomic, surgical, procedural, range of motion, fixation, stabilization or other outcome risks based on measurements of one or more of a plurality of factors.

In one embodiment, the computer implemented interactive patient specific surgical planning system includes instructions for a step in a pre-operative total joint planning method for comparison of anatomic or reverse shoulder surgery implants or guides where the anterior edge of a glenoid implant is aligned with an anterior edge of a glenoid bone. In one embodiment, the computer implemented interactive patient specific surgical planning system includes instructions for a step in a pre-operative total joint planning method for comparison of anatomic or reverse shoulder surgery implants or guides where the retroversion of a glenoid implant is adjusted.

In one embodiment, the computer implemented interactive patient specific surgical planning system includes instructions for a step in a pre-operative total joint planning method for comparison of anatomic or reverse shoulder surgery implants or guides where the augmentation of a glenoid implant is adjusted.

In one embodiment, the computer implemented interactive patient specific surgical planning system includes instructions for a step in a pre-operative total joint planning method for comparison of anatomic or reverse shoulder surgery implants or guides where the inferior tilt of a glenoid implant is adjusted.

In one embodiment, the computer implemented interactive patient specific surgical planning system includes instructions for a step in a pre-operative total joint planning method for comparison of anatomic or reverse shoulder surgery implants or guides where bone support for a glenoid implant and/or a humeral implant is evaluated.

In one embodiment, the computer implemented interactive patient specific surgical planning system includes instructions for a step in a pre-operative total joint planning method for comparison of anatomic or reverse shoulder surgery implants or guides where the medialization of a glenoid implant is adjusted by assessing the volumetric amount of bone needed to be removed by reaming.

In one embodiment, the computer implemented interactive patient specific surgical planning system includes instructions for a step in a pre-operative total joint planning method for comparison of anatomic or reverse shoulder surgery implants or guides where fixation support in the absence of central pegs that penetrate a vault medially is analyzed.

In one embodiment, the computer implemented interactive patient specific surgical planning system includes instructions for a step in a pre-operative total joint planning method for comparison of anatomic or reverse shoulder surgery implants or guides where a joint line is analyzed by comparing an original joint line and a new joint line.

In one embodiment, the computer implemented interactive patient specific surgical planning system includes instructions for a step in a pre-operative total joint planning method for comparison of anatomic or reverse shoulder surgery implants or guides where widths of the glenoid implant and the glenoid bone are measured and matched after reaming and aligning inferior and superior axes of the glenoid implant and bone and including similar appropriate measuring and matching of the humeral implant.

In one embodiment, the computer implemented interactive patient specific surgical planning system includes instructions for a step in a pre-operative total joint planning method for comparison of anatomic or reverse shoulder surgery implants or guides where the diameter of a humeral head is determined.

In one embodiment, the computer implemented interactive patient specific surgical planning system includes instructions for a step in a pre-operative total joint planning method for comparison of anatomic or reverse shoulder surgery implants or guides where the height of a humeral head is determined.

In one embodiment, the computer implemented interactive patient specific surgical planning system includes instructions for a step in a pre-operative total joint planning method for comparison of anatomic or reverse shoulder surgery implants or guides where the size of a humeral or glenoid implant is measured by computed tomography scan or other appropriate medical imaging modality.

In one embodiment, the computer implemented interactive patient specific surgical planning system includes instructions for a step in a pre-operative total joint planning method for comparison of anatomic or reverse shoulder surgery implants or guides where a best fit size of a humeral implant or a glenoid implant from a range of sizes from one or more medical component manufacturers is determined.

In one embodiment, the computer implemented interactive patient specific surgical planning system includes instructions for a step in a pre-operative total joint planning method for comparison of anatomic or reverse shoulder surgery implants or guides where vectors are compared in three dimensions to measure the distance of relocation of humeral tuberosity compared to the scapula.

In one embodiment, the computer implemented interactive patient specific surgical planning system includes instructions for a step in a pre-operative total joint planning method for comparison of anatomic or reverse shoulder surgery implants or guides where range of motion analysis is conducted, including virtually positioning implants through extreme ranges of motion to measure impact locations and compensate for necessary functional range of motion based on activities of daily living and standard clinical assessments.

In one embodiment, the computer implemented interactive patient specific surgical planning system includes instructions for a step in a pre-operative total joint planning method for comparison of anatomic or reverse shoulder surgery implants or guides where soft tissue analysis comprising determining key soft tissue insertion points is conducted.

In one embodiment, the computer implemented interactive patient specific surgical planning system includes instructions for a step in a pre-operative total joint planning method for comparison of anatomic or reverse shoulder surgery implants or guides where penetration of the cortical wall anteriorly of the vault is assessed.

In one embodiment, the computer implemented interactive patient specific surgical planning system includes instructions for a step in a pre-operative total joint planning method for comparison of anatomic or reverse shoulder surgery implants or guides where the width of the greater tuberosity to medial head edge with an implant is compared to the anatomic width.

In one embodiment, the computer implemented interactive patient specific surgical planning system includes instructions for a step in a pre-operative total joint planning method for comparison of anatomic or reverse shoulder surgery implants or guides for viewing or displaying one or more anatomic views including, optionally, indications of coronial, sagittal and transverse anatomical planes for the viewing of a glenoid implant or a humeral implant; views of a glenoid implant with patient-specific back-side augmentation; views of an exemplary glenoid implant with patient-specific augmentation; views of involved joint bone or a scapula bone and glenoid surface having depicted indicia of one or more factors assessed by the planning system for comparison; views of a scapula with a humerus bone having a selected implant and surgical procedure indicted; views of a glenoid implant with no back-side augmentation and view of a glenoid implant with back-side augmentation; and/or views of patient-specific humerus or glenoid implants each having views of customized affixation components.

Figure 9A:
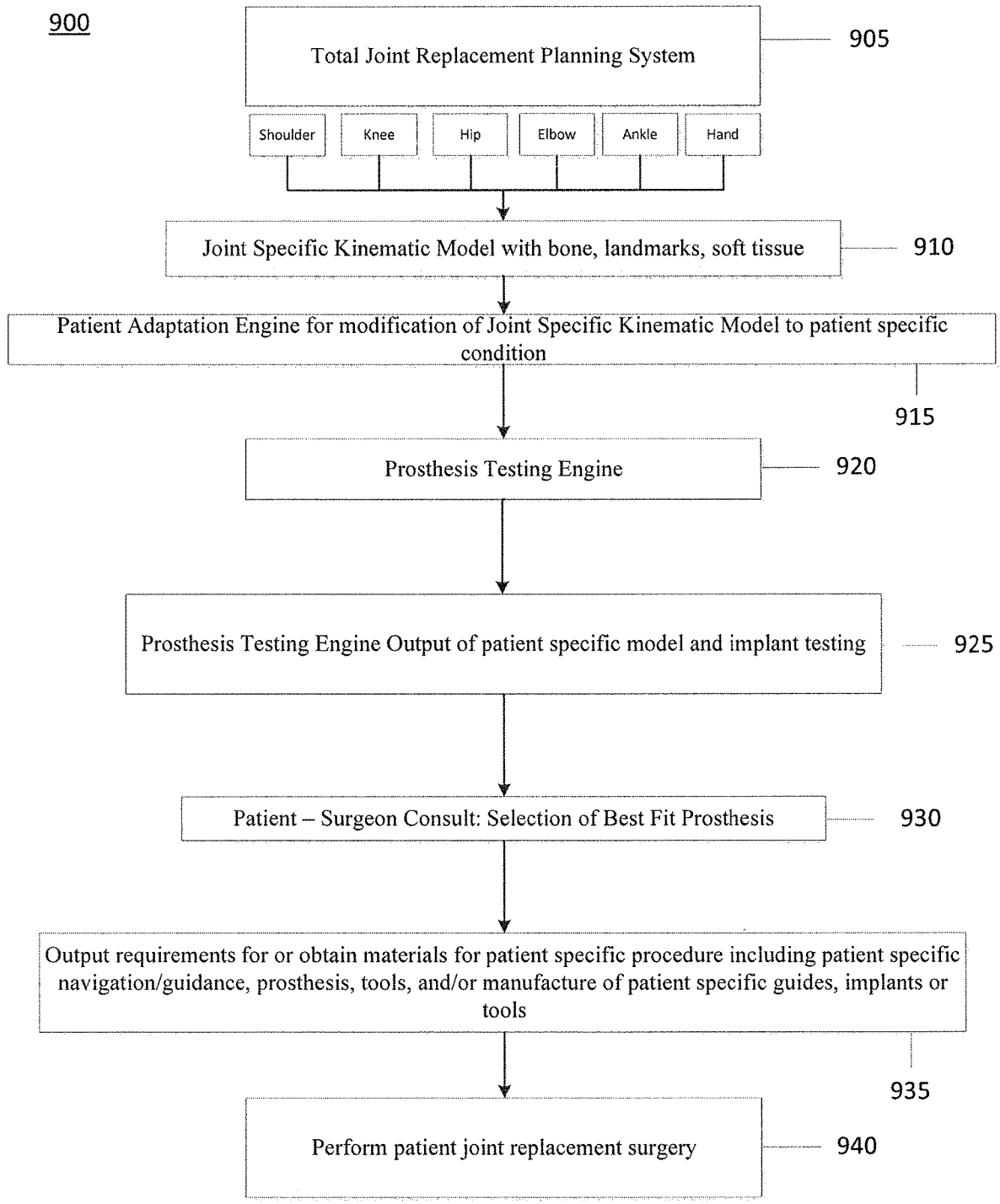
FIG. 9A is a flow chart of an exemplary computer implemented method of utilizing a total joint surgical planning and evaluation system.
Figure 9B:
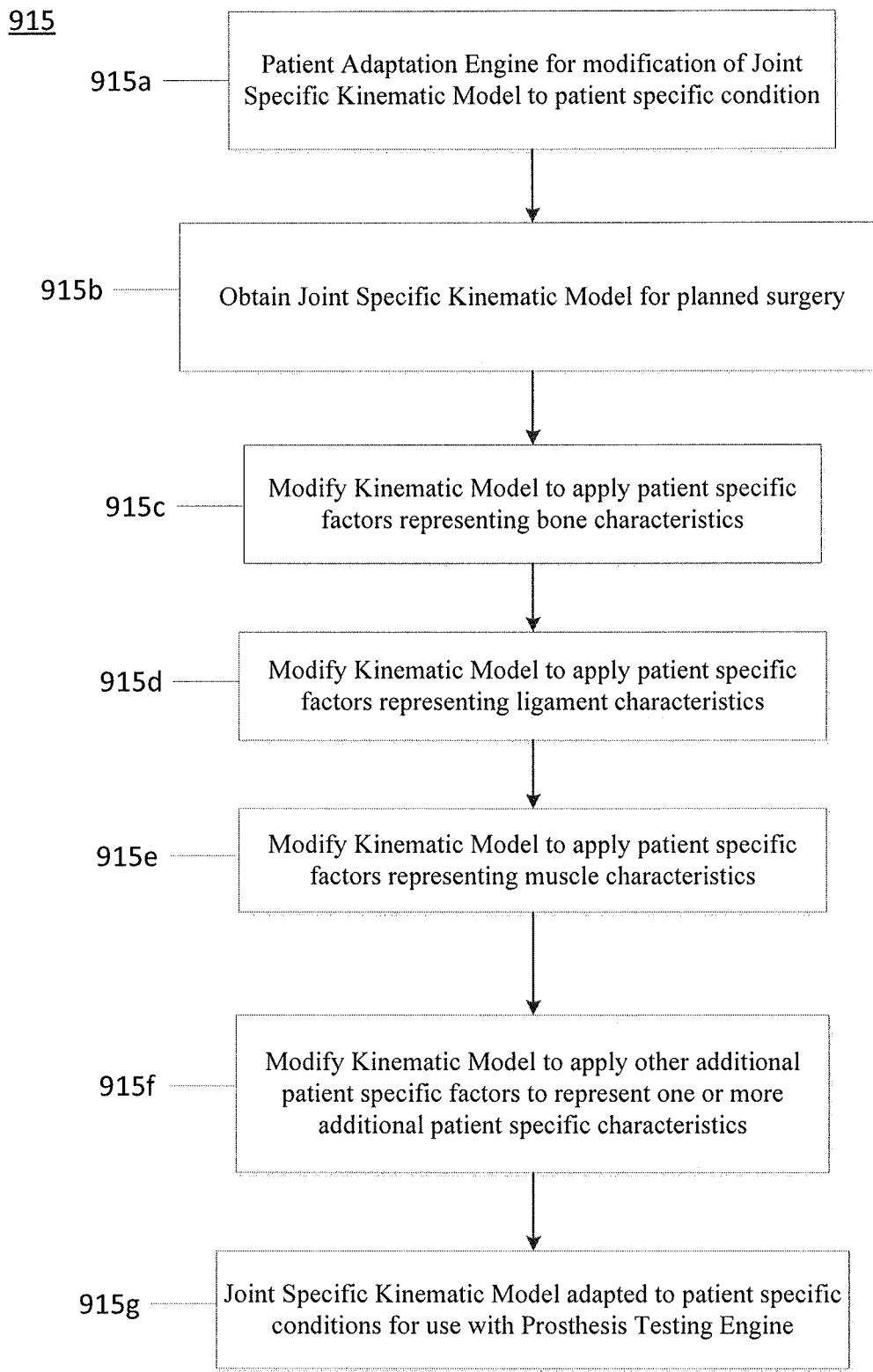
FIG. 9B is a flow chart of additional steps for operation of a patient adaptation engine as performed within a computer implemented method of operating a total joint replacement planning system of FIG. 9A.
Figure 9C:
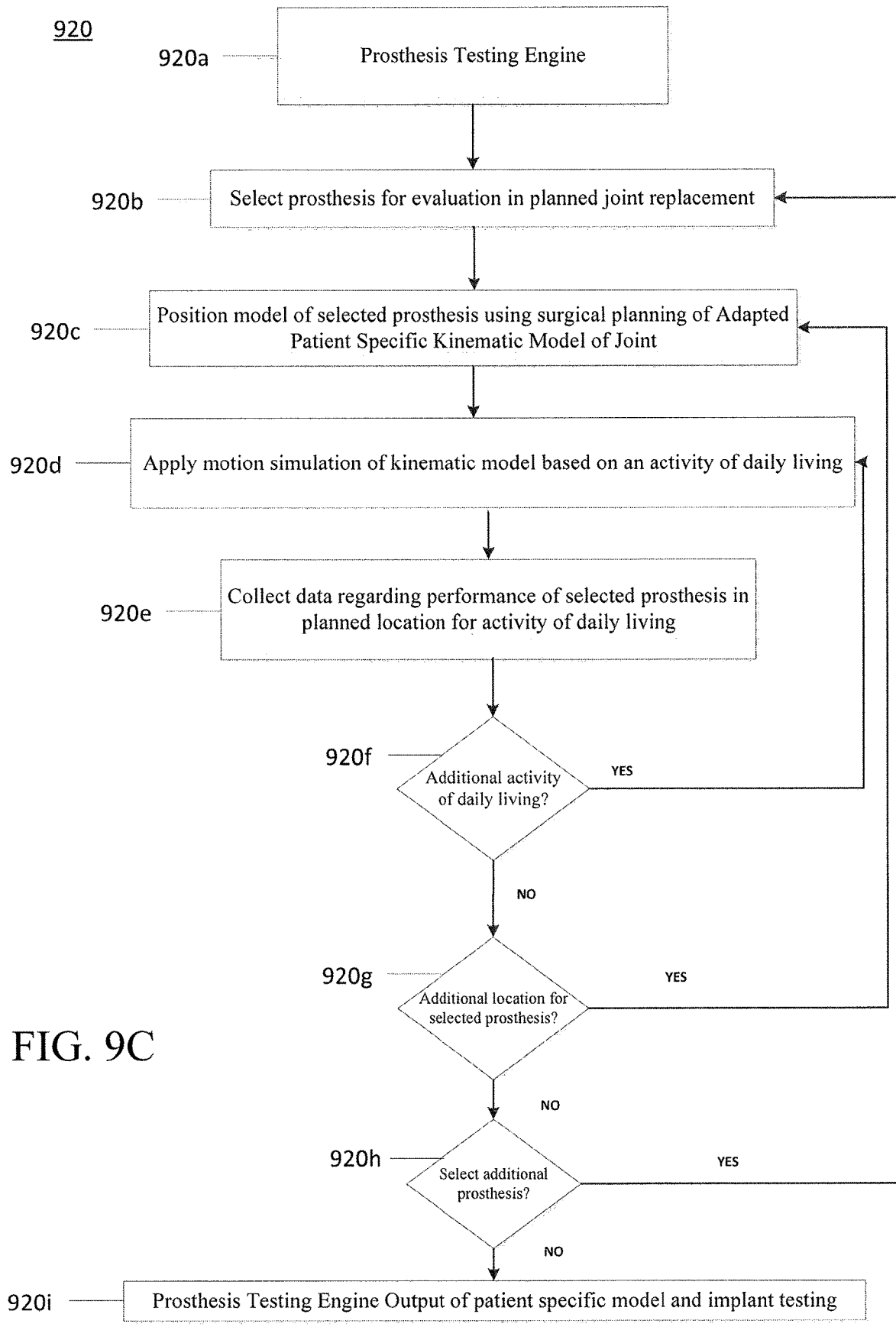
FIG. 9C is a flow chart of additional steps for operation of a prosthesis testing engine as performed within a computer implemented method of operating a total joint replacement planning system of FIG. 9A.

FIGS. 9A, 9B and 9C relate to a method of utilizing a total joint replacement planning system. FIG. 9A describes a total joint surgical planning method 900. FIG. 9B details a method 920 of aspects of a prosthesis testing engine. FIG. 9C details a method 915 of the use of a patient adaptation engine.

FIG. 9A details the steps of a method 900 for operating a computer implemented Total Joint Replacement Planning System 905. The Total Joint Replacement Planning System may be used for total or partial joint replacement for a surgery planned and performed on a shoulder, a knee, a hip, an ankle, an elbow, a wrist, a hand or the joints of the fingers and thumb, and a foot or the joints of the toes.

Next, at step 910, an electronic, computer rendered or virtual joint specific kinematic model is obtained. As described herein, the kinematic model includes bone, landmarks, soft tissue including ligaments, cartilage and joint capsules. In addition, the kinematic model is suited for simulations of a wide range of motions of the joint for activities of daily living, clinical assessments or complex motions related to exercise, sports or athletic activities.

Next, at step 915, there is the operation of a patient adaptation engine. The operation of the patient adaptation engine provides for modification of the joint specific kinematic model to be modified to one or more patient specific conditions. Operation of the patient adaptation engine prepares the general joint specific kinematic model for use with patient specific surgical planning for total or partial joint replacement.

Next, at step 920, the prosthesis testing engine is prepared for operation in order to simulate the selected prosthesis or implants or tools to be used in a total or partial joint surgery under evaluation using the total joint replacement planning system 905.

Next, at step 925, the prosthesis testing engine provides outputs of the patient specific model and the various implant testing performed.

Next, at step 930, the patient and surgeon conduct a medical consult using outputs from step 925. During the consult, there is a selection of a best fit prosthesis for use in a total or a partial joint surgery based on the outputs provided by the testing conducted in steps 915-925.

Next, at step 935, there is a process for obtaining the materials needed for the evaluated partial or total joint surgery. The total joint replacement planning system may provide an output including the requirements for or to obtain materials for patient specific procedures as evaluated in the system. Surgical materials for the patient specific total or partial joint procedure include, for example, patient specific navigation guidance tools, prosthesis, surgical tools and/or the manufacture of one or more patient specific guides, implants or tools.

Finally, at step 940, the joint replacement surgery evaluated and planned using steps of method 900 is performed.

FIG. 9B includes additional details of the patient adaptation engine (915) described above in the method 900. First, at step 915a, there is a step of initializing the patient adaptation engine. The patient adaptation engine modifies a joint specific kinematic model to include patient specific conditions including those obtained from patient specific imaging, clinical evaluation, testing and the like. Next, at step 915b, obtain a joint specific kinematic model for the planned surgery for evaluation using the total joint replacement planning system.

Next, at step 915c, modify the kinematic model to apply patient specific factors representing bone characteristics.

Next, at step 915d, modify the kinematic model to apply patient specific factors representing ligament characteristics.

Next, at step 915e, modify the kinematic model to apply patient specific factors representing muscle characteristics.

Next, at step 915f, modify the kinematic model to apply other additional patient specific factors representing one or more additional patient specific characteristics related to the total or partial joint surgery under evaluation.

Finally, at step 915g, the method 915 is completed and the joint specific kinematic model is adapted to contain patient specific conditions and ready for use with the prosthesis testing engine to evaluate different implants and surgical positions as described herein as part of the total joint replacement planning system.

FIG. 9C provides a method 920 that further explains the steps performed by the prosthesis testing engine 920 in method 900 (FIG. 9A). First, at step 920a, the prosthesis testing engine is initiated. Next, at step 920b, there is a step of electing a prosthesis for evaluation and a plan joint replacement. Next, at step 920c, there is the step to position a model of the selected prosthesis using the surgical planning within the adapted patient specific kinematic model of the joint. During this step, a virtual surgery is performed to position the selected prosthesis within the patient specific kinematic model of the joint under evaluation.

Next, at step 920d, the process of applying motion simulation of the patient specific kinematic model based on an activity of daily living. During this step, the selected prosthesis in the selected surgical location is evaluated while the motion of an activity of daily living is imparted to the patient specific model. Data reflecting the performance of the selected prosthesis in the planned surgical location for the selected activity of daily living is collected at step 920e.

Next, the decision point 920f allows for an additional activity of daily living to be evaluated for the selected prosthesis and surgical site. If the answer decision point 920f is "YES" then the method loops back to step 920d to allow for another activity of daily living to be selected and simulated according to step 920d and data collected according to step 920e.

If the answer decision point 920f is "NO" then the method proceeds to decision point 920g. Decision 920g allows for the selected prosthesis to be moved into a different additional location for evaluation. If the answer to decision point 920g is "YES" then the method loops back to step 920c for a new location and then repeats activity and data collection according to steps 920d and 920e along with repeating steps for additional activities (step 920f).

If the answer to decision point 920g is "NO" then the method proceeds to step 920h to allow for another prosthesis to be tested in the system. If the answer to the decision point 920h is "YES" then the method loops back to step 920b so that an additional implant may be selected for evaluation. The method would proceed to repeat step 920c for a new location and then repeats activity and data collection according to steps 920*d* and 920*e* along with repeating steps for additional locations of the newly selected prosthesis (step 920*g*).

If the answer to the decision point 920*h* is "NO" then the method continues to step 920*i*. Step 920*i* is the output provided by the prosthesis testing engine that includes the results of all simulations performed by the patient specific model including all implants tested, all surgical sites evaluated and the results of all motions imparted by simulated activities of daily living. These various outputs are provided to and utilized during step 925 (see FIG. 9A).

Embodiments of the total joint replacement planning system enable a wide range of methods of treating a patient, and/or surgical methods, are provided wherein one or more of the disclosed methods of analysis and optimization are performed on a patient in need of partial or complete joint surgery. In some embodiments, methods of treating a patient are provided wherein a disclosed method of analysis and optimization is performed, an optimized guide is designed and created, and one or more joint specific implants are designed, created, and/or selected. In some embodiments, a method of treating a patient can comprise utilizing the pre-operative planning to design and optimize a guide and one or more joint specific implants, and the use of the guide to surgically implant the one or more joint specific prosthetic devices according to a selected joint specific surgical procedure. Various embodiments of the inventive patient specific surgical planning system described herein may be adapted for any of a wide variety of joints. Additionally, a partial or total joint surgery may include a surgery planned and performed on a shoulder, a knee, a hip, an ankle, an elbow, a wrist, a hand or the joints of the fingers and thumb, and a foot or the joints of the toes.

The presently disclosed subject matter provide methods, systems and devices for virtual pre-operatively planned total or partial joint implants and prosthetic devices for total or partial joint surgeries while also accounting for range of motion desired for activities of daily living and/or standard clinical assessments of range of motion. The presently disclosed subject matter also provides for planned methods including patient specific instruments for the surgical preparation and implantation of total or partial joint implants in patients undergoing total or partial joint surgery.

Further, in some aspects of the disclosed methods, systems and devices, a computer readable medium can be provided having stored thereon executable instructions that when executed by a processor of a computer can control the computer to generate a virtual 3D model of a patient-specific, i.e. customized, augmented total or partial joint specific implant and/or an appropriate surgical placement guide device reflecting one or more optimized parameters determined during pre-operative planning. Thus, in some embodiments a computer readable medium is provided, wherein the computer readable medium has stored thereon executable instructions that when executed by the processor of a computer control the computer to perform one or more of the planning method and/or analysis steps as disclosed herein.

It should be noted that the computers, computing devices, hardware and/or functionality described herein may constitute a special purpose test device. Further, computers, computing devices, hardware and/or functionality described herein can improve the technological field of pre-operative planning for joint specific surgery and can improve generation of virtual modeling systems including those with interfaces to patient specific kinematic and biometric modeling.

The subject matter described herein for generating 3D models of total or partial joint specific implant devices, and/or for modeling and virtually simulating pre-operative total or partial joint surgery analysis improves the likelihood of a positive outcome from total or partial joint surgery. It should also be noted that a computing platform, computer, computing device, and/or hardware that implements the subject matter described herein may comprise a special purpose computing device usable to generate 3D models of joint specific implant devices, and/or for modeling and virtually simulating pre-operative total or partial joint surgery analysis.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments a computer readable medium is provided, having stored thereon executable instructions that when executed by the processor of a computer control the computer to perform steps comprising generating a virtual three dimensional model of a joint specific guide reflecting one or more optimized parameters determined during pre-operative planning based on the above method steps. In some embodiments, a computer readable medium is provided, having stored thereon executable instructions that when executed by the processor of a computer control a 3D printing device in communication with the computer, whereby the 3D printing device prints a joint specific guide, or placement guide, for use in joint specific replacement surgery in a patient for which the optimization analysis was conducted.

In some embodiments, provided herein are pre-operative planning and joint surgery kits for each selected total or partial joint procedure. Such kits can in some aspects comprise a set of instructions for performing pre-operative analysis steps as disclosed herein, and one or more guides, total or partial joint prosthetic devices. In some embodiments, a kit can comprise a 3-D printing device for producing a guide and/or one or more joint specific prosthetic devices. In some embodiments, a kit can comprise a computer-readable medium for use in conducting the pre-operative planning, and designing a guide, a joint specific implant based on input parameters gathered during the pre-operative planning. In some embodiments, the devices are customizable and/or modular in design such that the prosthetic device can be optimized for the patient based on the pre-operative planning analysis of the joint undergoing surgical evaluation. In some aspects, a kit can comprise a range of joint specific implants with or without having an augmented portion. In an augmented implant is selected, then the augmentation is selectable—as appropriate to the surgical technique for the selected joint—in terms of the augmentation size, shape, and position, both in the superior/inferior and posterior/anterior position. In some embodiments, a kit comprising a range of joint specific implants having one or more or an augmented portion is provided where the augmentation is selectable in terms of its size, shape, and position, where the position is defined by an angular and a radial position as is appropriate for the joint under consideration.

In some embodiments, the methods described herein of designing and/or creating implantable components for a patient specific partial or total joint surgical procedures including a joint specific implant component, a joint surgery guide, including a joint implant placement guide based on or derived using pre-operative planning including patient specific bone, muscle and soft tissue along with a partial or total joint kinematics can further comprise one or more optimization steps. Such optimization steps can comprise the identification of anatomic, surgical, procedural, range of motion, fixation, stabilization or other outcome risks based on measurements of one or more of a plurality of factors related to the total or partial joint surgery under evaluation, the specific patient or a surgeon specific recommendation.

In one embodiment, the computer implemented interactive patient specific surgical planning system includes instructions for a step in a pre-operative total joint planning method for comparison of joint specific surgery implants or guides. In one embodiment, the computer implemented interactive patient specific surgical planning system includes instructions for a step in a pre-operative total joint planning method for comparison of joint specific surgery implants or guides including accommodations for user based adjustments.

In one embodiment, the computer implemented interactive patient specific surgical planning system includes instructions for a step in a pre-operative total joint planning method for comparison of joint specific surgery implants or guides where the augmentation of an implant or a proposed surgical site is adjusted.

In one embodiment, the computer implemented interactive patient specific surgical planning system includes instructions for a step in a pre-operative total joint planning method for comparison of joint specific surgery implants or guides where the implant is rotated, tilted, shifted, off set or otherwise adjusted with respect to a patient specific surgical site.

In one embodiment, the computer implemented interactive patient specific surgical planning system includes instructions for a step in a pre-operative total joint planning method for comparison of joint specific surgery implants or guides where bone support for a total or partial joint implant is evaluated.

In one embodiment, the computer implemented interactive patient specific surgical planning system includes instructions for a step in a pre-operative total joint planning method for comparison of joint specific surgery implants or guides where the placement of an implant is adjusted by assessing the volumetric amount of bone needed to be removed by reaming or otherwise adapting a bone for accepting an implant as part of a total or partial joint surgery.

In one embodiment, the computer implemented interactive patient specific surgical planning system includes instructions for a step in a pre-operative total joint planning method for comparison of joint specific surgery implants or guides where a joint line is analyzed by comparing an original joint line and a new joint line.

In one embodiment, the computer implemented interactive patient specific surgical planning system includes instructions for a step in a pre-operative total joint planning method for comparison of joint specific surgery implants or guides where widths or other relevant dimensions of the joint implant and the implant receiving bone are measured and matched after reaming and aligning inferior and superior axes of the implant and bone and including similar appropriate measuring and matching of any other components used in the total or partial joint procedure under evaluation.

In one embodiment, the computer implemented interactive patient specific surgical planning system includes instructions for a step in a pre-operative total joint planning method for comparison of joint specific surgery implants or guides where a diameter or other relevant geometric measure of a specific anatomical portion of the total joint under evaluation is determined or measured.

In one embodiment, the computer implemented interactive patient specific surgical planning system includes instructions for a step in a pre-operative total joint planning method for comparison of joint specific surgery implants or guides where the size of a joint specific implant is measured by computed tomography scan or other appropriate medical imaging modality as part of an assessment or evaluation of a patient specific surgical model.

In one embodiment, the computer implemented interactive patient specific surgical planning system includes instructions for a step in a pre-operative total joint planning method for comparison of joint specific surgery implants or guides where a best fit size of a total joint or partial joint implant is provided or selected from a range of sizes available from one or more medical component manufacturers.

In one embodiment, the computer implemented interactive patient specific surgical planning system includes instructions for a step in a pre-operative total joint planning method for comparison of joint specific surgery implants or guides where range of motion analysis is conducted, including virtually positioning implants through normal as well as extreme ranges of motion to measure impact locations and compensate for necessary functional range of motion based on activities of daily living and standard clinical assessments. As used herein, activities for daily living may include motions, actions or complex multi joint maneuvers including limbs and joints other than the joint under evaluation for a total or partial surgical procedure. In one example, the motions or actions evaluated under activities of daily living include sport or athletic activities performed by the patient being evaluated for partial or total joint surgery.

In one embodiment, the computer implemented interactive patient specific surgical planning system includes instructions for a step in a pre-operative total joint planning method for comparison of joint specific surgery implants or guides where soft tissue analysis comprising determining key soft tissue insertion points is conducted.

In one embodiment, the computer implemented interactive patient specific surgical planning system includes instructions for a step in a pre-operative total joint planning method for comparison of joint specific surgery implants or guides for viewing or displaying one or more anatomic views including, optionally, indications of coronial, sagittal and transverse anatomical planes for the viewing of a total joint implant or a partial joint implant; views of a joint specific implant with patient-specific back-side augmentation; views of an exemplary joint specific implant with patient-specific augmentation; views of an involved partial or total joint bone or a joint surface having depicted indicia of one or more factors assessed by the planning system for comparison; views of a joint bone having a selected implant and surgical procedure indicted; views of a joint implant with no back-side augmentation and view of a joint implant with back-side augmentation; and/or views of patient-specific total or partial joint implants each having views of customized affixation components.

In various alternative embodiments of the total joint surgical systems and methods described herein, a patient can comprise a mammalian subject. In other embodiments, a patient can be a male human subject or a female human subject, including an adult, an adolescent or a child.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the terms "patient-specific," "customized," and/or "adaptive," when used in reference to a glenoid implant or humeral implant, can be used interchangeably and can in some embodiments refer to the specialization of such features taking into consideration factors specific to a patient to be treated, including for example characteristics acquired from pre-operative analysis and planning or a selected reverse or anatomic shoulder procedure.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A pre-operative planning method for a computer implemented interactive patient specific surgical planning system, the method comprising:
    obtaining a joint specific kinematic model of a joint of a patient to be evaluated for a total joint or a partial joint surgical procedure;
    operating a patient adaptation engine to modify at least one of bone, soft tissue or landmarks in the joint specific kinematic model to render a patient specific kinematic model by adapting the joint specific kinematic model to include one or more patient specific conditions;
    operating a prosthesis testing engine to electronically perform a total or a partial joint surgery to position a selected implant in the patient specific kinematic model and to simulate motion of the patient joint with the selected implant while performing an activity of daily living;
    providing an output of the results of the operating a patient adaptation engine and operating a prosthesis testing engine; and
    selecting an actual implant for a planned surgical procedure to be performed on the patient.

2. The method of claim 1 wherein the joint specific kinematic model is one of a shoulder, a knee, a hip, an ankle, an elbow, a wrist, a hand or the joints of the fingers and thumb, and a foot or the joints of the toes.

3. The method of claim 1 the step of operating a patient adaptation engine wherein the one or more patient specific conditions include a patient specific condition obtained from patient specific imaging, clinical evaluation, or testing.

4. The method of claim 1 further comprising modifying the kinematic model by applying one or more patient specific factors representing a bone characteristic.

5. The method of claim 1 further comprising modifying the kinematic model by applying one or more patient specific factors representing a ligament characteristic.

6. The method of claim 5 wherein the operating a prosthesis engine step is performed after the modifying the kinematic model by applying one or more patient specific factors representing a ligament characteristic.

7. The method of claim 1 further comprising modifying the kinematic model by applying one or more patient specific factors representing a muscle characteristic.

8. The method of claim 7 wherein the operating a prosthesis engine step is performed after the modifying the kinematic model by applying one or more patient specific factors representing a muscle characteristic.

9. The method of claim 1 further comprising modifying the kinematic model by applying one or more patient specific factors representing a soft tissue or cartilage or a joint capsule or a portion of a joint capsule or patient specific fibrous or scar tissue.

10. The method of claim 9 wherein the operating a prosthesis engine step is performed after the modifying the kinematic model by applying one or more patient specific factors representing a soft tissue or cartilage or a joint capsule or a portion of a joint capsule or patient specific fibrous or scar tissue.

11. The method of claim 1 further comprising modifying the kinematic model by applying one or more patient specific factors representing one or more additional patient specific characteristics related to the total or partial joint surgery under evaluation.

12. The method of claim 1 the one or more additional patient specific characteristics related to the total or partial joint surgery under evaluation comprising a patient specific activity for daily living, a patient specific post-surgery sporting activity or a patient specific range of motion selected for intended return to active post-surgical lifestyle.

13. The method of claim 1 the step of operating a prosthesis testing engine further comprising the step of electing a digital model of a prosthesis for evaluation.

14. The method of claim 13 further comprising performing a virtual surgery to position the selected prosthesis within the patient specific kinematic model of the joint under evaluation.

15. The method of claim 13 further comprising the step of applying motion simulation of the patient specific kinematic model based on an activity of daily living wherein the selected prosthesis in the selected surgical location is evaluated while the motion of an activity of daily living is imparted to the patient specific model.

16. The method of claim 15 wherein the process of simulating the activities of daily living is repeated for daily grooming, self-care and at least one athletic or sporting activity.

17. The method of claim 16 further comprising moving the selected prosthesis to a different location within the patient specific kinematic model and repeating the step of applying motion simulation of the patient specific kinematic model based on an activity of daily living.

18. The method of claim 17 further comprising providing an output from the prosthesis testing engine that includes the results of all simulations performed by the patient specific model including all implants tested, all surgical sites evaluated and the results of all motions imparted by simulated activities of daily living.

19. The method of claim 1 further comprising a step to position a model of the selected prosthesis using the surgical planning within the adapted patient specific kinematic model of the joint.

20. The method of claim 1 wherein the activity for daily living is one or more pre-surgical, patient requested specific activities related to performance of a post-surgical activity related to performance of an occupation, a sporting activity, an outdoor activity or a recreational activity.

* * * * *